(12) United States Patent
Rumsey

(10) Patent No.: US 8,356,598 B2
(45) Date of Patent: Jan. 22, 2013

(54) APPARATUS AND RELATED METHOD FOR PROVIDING A PASSAGE INTO THE BODY

(75) Inventor: Royce Rumsey, Laguna Beach, CA (US)

(73) Assignee: Pyng Medical Corp., Richmond (CA)

( * ) Notice: Subject to any disclaimer, the term of this patent is extended or adjusted under 35 U.S.C. 154(b) by 1357 days.

(21) Appl. No.: 12/043,849

(22) Filed: Mar. 6, 2008

(65) Prior Publication Data

US 2008/0257359 A1 Oct. 23, 2008

Related U.S. Application Data

(60) Provisional application No. 60/923,856, filed on Apr. 17, 2007.

(51) Int. Cl.
*A61M 11/00* (2006.01)
(52) U.S. Cl. .................................. 128/207.29; 606/167
(58) Field of Classification Search ............. 128/207.29, 128/207.14, 200.26; 606/167–171
See application file for complete search history.

(56) References Cited

U.S. PATENT DOCUMENTS

| | | | |
|---|---|---|---|
| 3,817,250 A * | 6/1974 | Weiss et al. ............... | 128/207.29 |
| 3,893,454 A * | 7/1975 | Hagelin ....................... | 600/219 |
| 4,520,810 A | 6/1985 | Weiss | |
| 4,677,978 A | 7/1987 | Melker | |
| 4,877,021 A * | 10/1989 | Higer et al. ............... | 128/200.26 |
| 4,978,334 A | 12/1990 | Toye | |
| 5,217,005 A | 6/1993 | Weinstein | |
| 5,988,168 A * | 11/1999 | Bair ........................ | 128/207.29 |
| 7,169,129 B2 * | 1/2007 | Gooden ................... | 604/164.02 |
| 7,308,896 B2 * | 12/2007 | Cruz ........................ | 128/207.29 |
| 7,631,642 B2 * | 12/2009 | Freitag et al. ............ | 128/200.26 |
| 2006/0070628 A1* | 4/2006 | Byatt et al. ............... | 128/207.29 |
| 2009/0229602 A1* | 9/2009 | Single, Jr. ................ | 128/200.26 |

FOREIGN PATENT DOCUMENTS

GB 2428201 1/2007

OTHER PUBLICATIONS

Exam Report from corresponding EP application No. 08745781.8.
Rusch, Rusch Quicktrach http://www.usemc.com/Rusch-Quicktrach-p/120900020.htm, Dec. 12, 2006, ( 1 page).

* cited by examiner

*Primary Examiner* — Steven Douglas
(74) *Attorney, Agent, or Firm* — Matthew A. Pequignot; Pequignot + Myers LLC

(57) ABSTRACT

An apparatus and method for providing a passage into the body for use in, among other things, medical procedures, including tracheostomies and cricothyroidectomies is described herein. In one embodiment, an apparatus for providing a passage into the body includes a first slider unit and a second slider unit operably connected to a slider track for retractable deployment of a scalpel and a tissue spreader attached respectively thereto, and for the auto-retraction of the scalpel due to movement of the second slider unit.

17 Claims, 24 Drawing Sheets

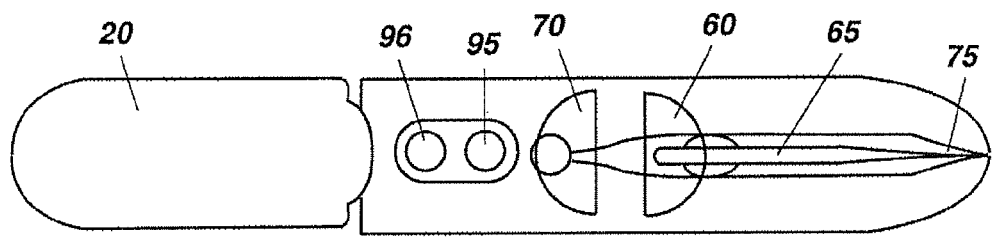
FIG. 4A
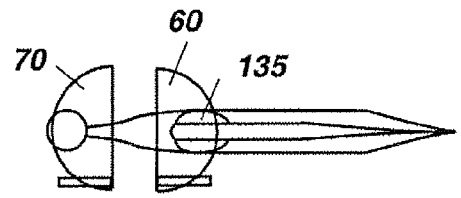
FIG. 4A1
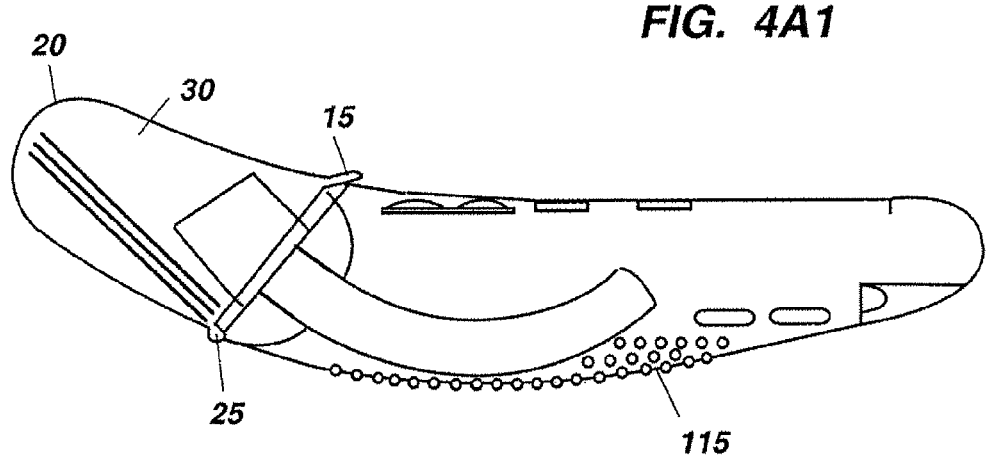
FIG. 4B
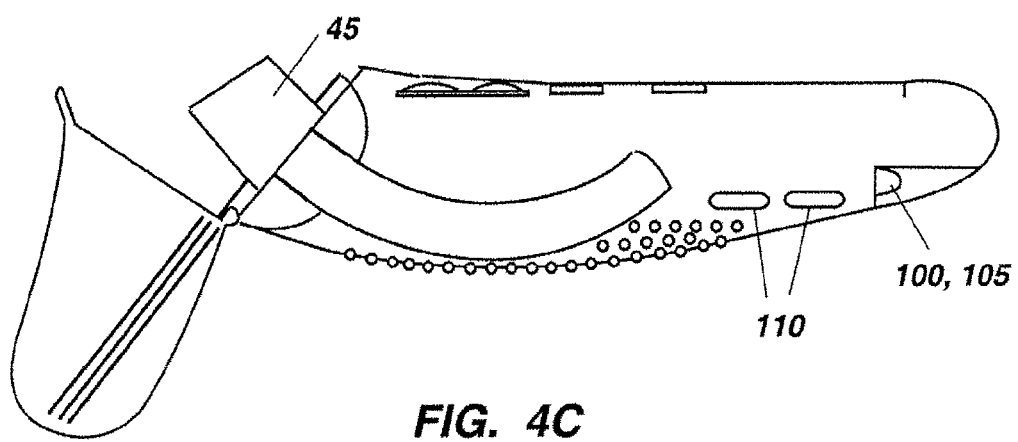
FIG. 4C

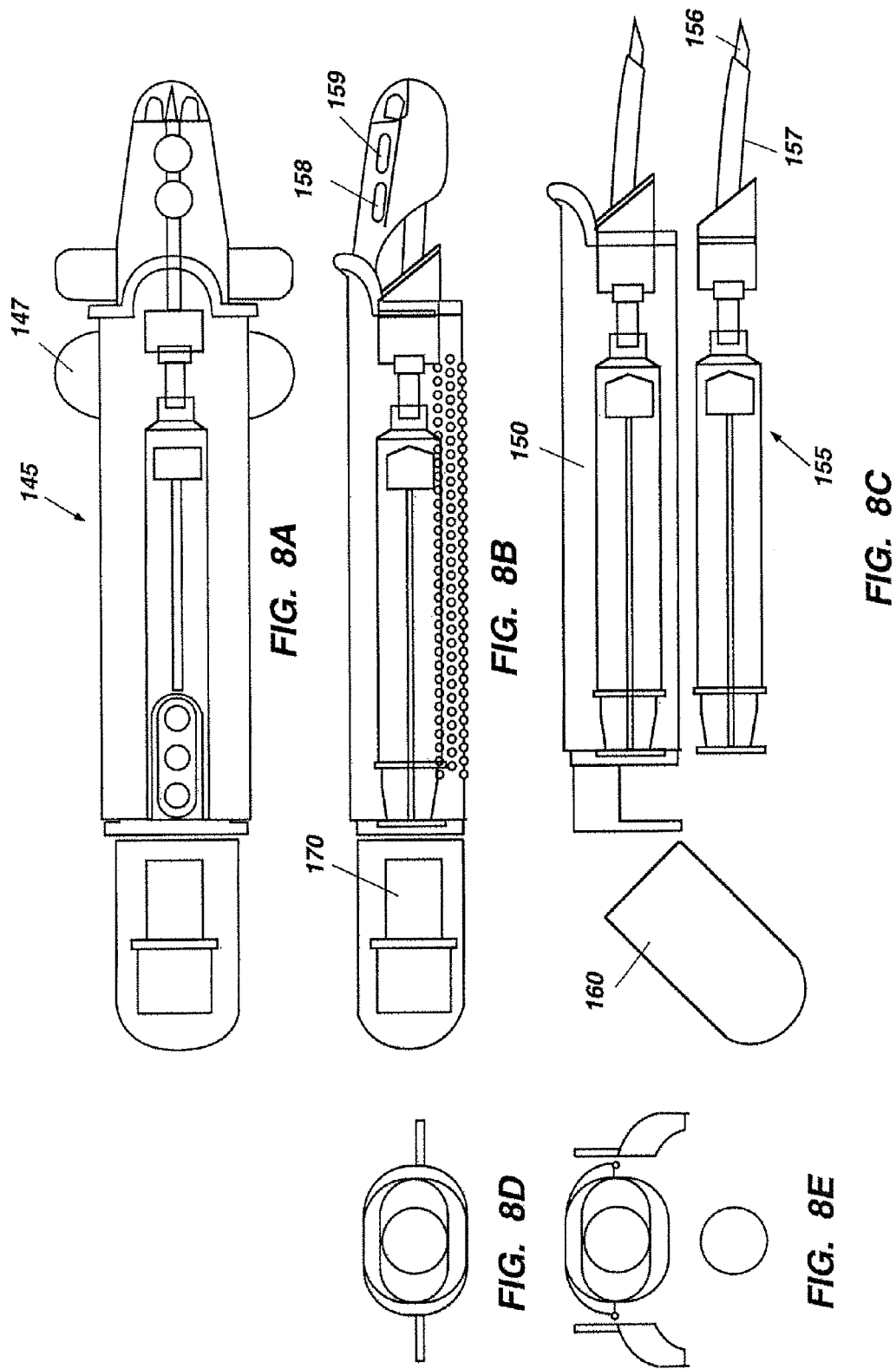

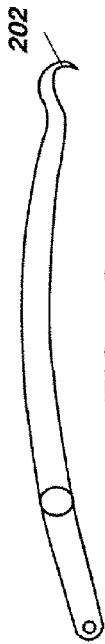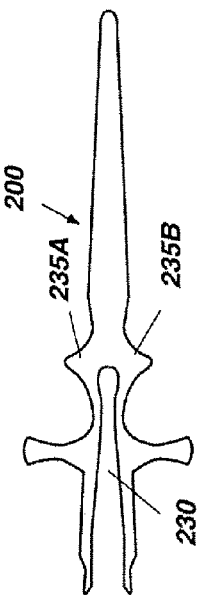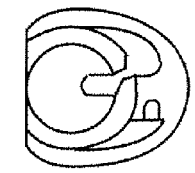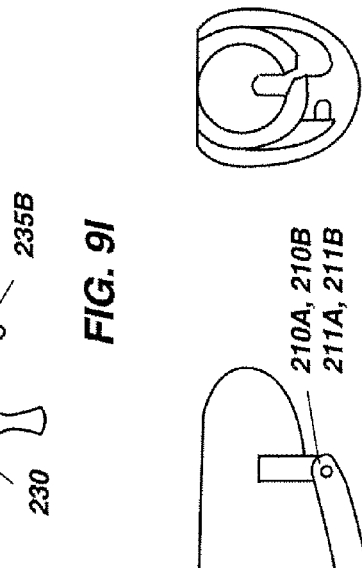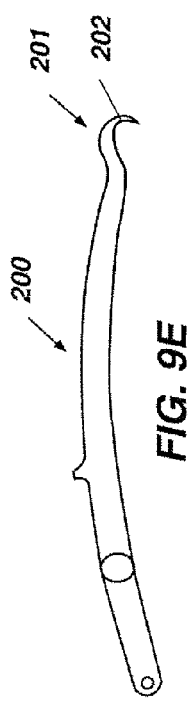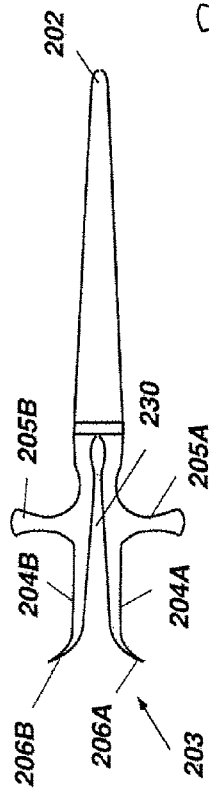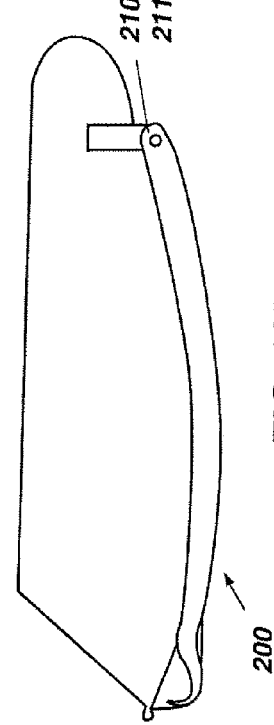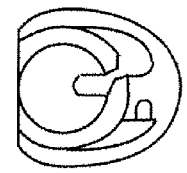

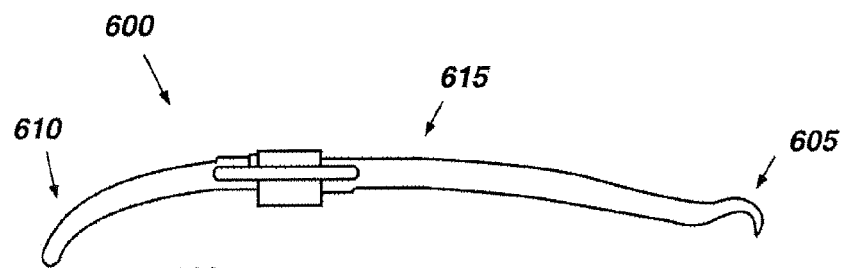
*FIG. 15A*
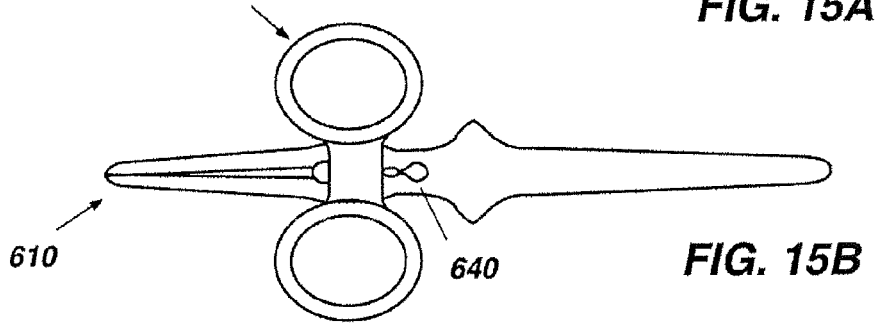
*FIG. 15B*
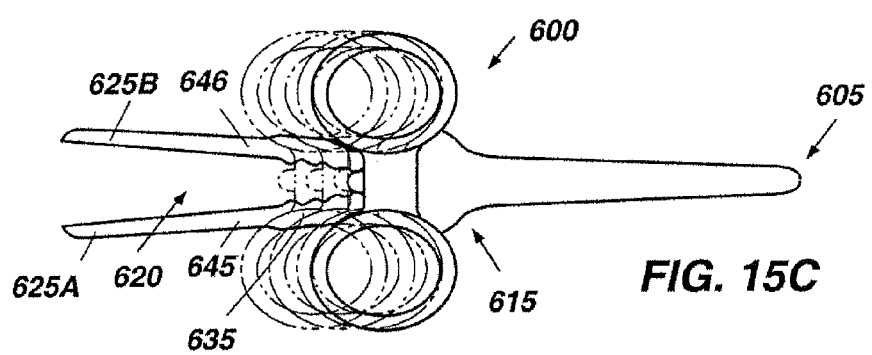
*FIG. 15C*
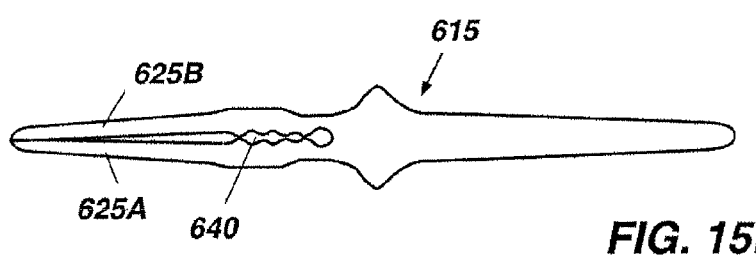
*FIG. 15D*
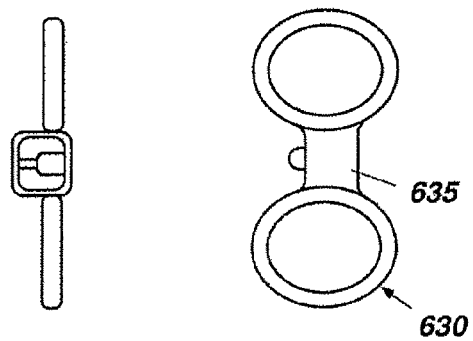
*FIG. 15F*  *FIG. 15E*

APPARATUS AND RELATED METHOD FOR PROVIDING A PASSAGE INTO THE BODY

CROSS-REFERENCE TO RELATED APPLICATION

This application claims priority under 35 U.S.C. §120 to provisional application No. 60/923,856 filed on Apr. 17, 2007, the contents of which are incorporated by reference in their entirety.

FIELD OF THE INVENTION

The disclosure relates generally to a surgical instrument such as an apparatus and method for providing a passage into the body, and more particularly, the disclosure relates to a percutaneous or a non-dissection apparatus and method for use in, among other things, establishing an airway in medical procedures including tracheostomies and cricothyroidectomies.

BACKGROUND OF THE INVENTION

In certain patient care situations, a first responder must immediately establish and maintain a patient's airway. Once an airway is established, the first responder must determine whether the patient is breathing. If breathing is adequate, maintenance of the airway should be continued. If breathing is inadequate, or absent, artificial respiration should be initiated.

Depending on among other things, the type and extent of an injury, various procedures and devices are available to assist in establishing an airway. Relatively less intrusive techniques for establishing an airway typically used in the absence of trauma include the head-tilt/chin-lift maneuver. With suspected trauma and/or an unconscious patient, a modified jaw thrust technique may be more appropriate to open the airway. Other methods for establishing an airway include the insertion of a nasopharayngeal airway, or in the case of a potentially life-threatening situation such as a complete upper airway obstruction the patient may require a tracheotomy or cricothyrotomy.

In this regard, a tracheotomy is generally defined as a temporary or permanent treatment for a variety of causes of breathing difficulties in which the creation of a new breathing pathway is required to by-pass the nose, mouth, and upper throat. A tracheotomy is usually considered when an endotracheal (ET) tube (a tube that goes in the throat through the mouth) will not be effective (in some emergency situations for example), or would be required for a long time. Sometimes, a tracheotomy is performed when an ET tube cannot be placed due to narrowing of the windpipe, blockage of the voice box (larynx) or facial trauma prevents intubation via the ET tube.

When an airway must be created immediately, a slightly different procedure called a cricothyroidotomy may be done. A cricothyrotomy (also called thyrocricotomy, cricothyroidotomy, inferior laryngotomy, intercricothyrotomy, coniotomy or emergency airway puncture) is an emergency incision through the skin and cricothyroid membrane to secure a patient's airway for emergency relief of upper airway obstruction. A cricothyrotomy is usually performed by paramedics and emergency physicians as a last resort in cases of severe choking due to upper airway obstruction when attempts at orotracheal and nasotracheal intubation have failed.

Preferably, when establishing an airway by a cricothyroidotomy (sometimes called a tracheotomy), percutaneous or non-dissection devices and techniques are normally preferably to dissection procedures, which require considerable more surgical skills in that many blood vessels are involved which tend to bleed profusely during a dissection procedure.

In this regard, combat casualty care, (that is, providing cricothyroidectomies in a field environment) continues to be a major challenge. Performing successful cricothyroidectomies has been identified as one of the three most important procedures for saving soldier's lives. Field cricothyroidectomies are critical to maintain life and provide severely injured far-forward battlefield participants an opportunity to survive until treated in a battlefield treatment facility. The current overall complication rate of a combat cricothyrotomy is 32% or 5 times higher than the complication rate when the procedure is conducted under controlled circumstances. Duress, adverse conditions, and non-standardization of airway kits all contribute to a high complication rate, including errors in incision location and incision depth in "combat care situations".

In this regard, fast, efficient, reliable, and effective emergency tracheotomies in support of combat casualty care in various field environments are currently not available due to, among other things, (1) lack of adequate and safe lighting, (2) too-deep tissue incisions that open both the trachea and esophageal tissue, (3) lack of device or means to directly and immediately displace incised tissue (4) non-standardization of airway medical kits, i.e., a wide variety of products and components are randomly and individually collected and loosely assembled among a variety of tracheosotomy medical kits (each kit being unique to the individual who assembled the kit), and (5) lack of easy access to necessary kit components.

The diversity and disparity in medical equipment, lack commonality of procedure/techniques resulting from the use of that equipment, and diminution of needed rapid component access, all contribute to confusion and loss of critical, life-saving time in the execution of emergency cricothyroidectomies in the field.

A currently available airway device includes the Rusch QuickTrach sold by a number of on-line distributors. Other airway devices include those described in U.S. Pat. No. 4,520,810 issued Jun. 4, 1985 to Weiss; U.S. Pat. No. 4,677,978 issued Jul. 7, 1987 to Melker; U.S. Pat. No. 4,978,334 issued Dec. 18, 1990 to Toye et al.; and U.S. Pat. No. 5,217,005 issued Jun. 8, 1993 to Weinstein, and the common #11 surgical scalpel and well-known endotracheal breathing tube.

Although each of the aforementioned devices provide for an airway into the body, none of the devices provide the combination of features of the subject matter described herein. Accordingly, it is desirable to provide a method and apparatus having universal and common components and safer and more expedient methodology of execution in providing an airway in medical procedures including tracheostomies and cricothyroidectomies under all emergency medical circumstances and environments.

SUMMARY OF THE INVENTION

The subject matter described herein relates generally to a surgical instrument such as an apparatus and method for providing a passage into the body and displacement (spreading) of incised tissue, and more particularly, to a percutaneous or a non-dissection apparatus and method having universal and common components and methodology of execution for use in, among other things, establishing an airway in medical procedures including tracheostomies and cricothyroidectomies.

In one embodiment, the device described herein for providing a passage into the body includes, a housing, and a scalpel and a tissue spreader disposed within the housing along a common slider track for extension and retraction (deployment) of the scalpel and the tissue spreader from the same side of the housing. The tissue spreader includes a bifurcated leading edge formed by a first arm and a second arm, and configured to move from a closed position to an open position upon retractable deployment of the tissue spreader to open a site of incision for acceptance of a breathing tube.

In another embodiment, an apparatus for providing a passage into the body, comprises a housing; a slider track formed within the housing; and a first slider unit configured to retain a scalpel and a second slider unit configured to retain a tissue spreader each operably connected to the slider track for movement along the slider track.

In still another embodiment, an apparatus for providing a passage into the body includes a first slider unit and a second slider unit operably connected to a slider track for retractable deployment of a scalpel and a tissue spreader attached respectively thereto, and for the auto-retraction of the scalpel due to movement of the second slider unit.

Furthermore, the device described herein for establishing an airway, provides, among other things, (1) visible and infrared light sources, (2) a combination of a clean retractable scalpel and a tissue spreader device, (3) incision depth gauging and regulation, (4) tissue preparation and administration components, (5) an endotracheal tube, and (6) a tube stabilization device all integrated into a durable, compact, lightweight, ergonomic hand-held device for one-hand operation (7) integrated tissue "hook" (commonly known and referred to as a "trach hook" for additional means of displacing incised tissue.

These and other embodiments will become readily apparent to those skilled in the art from the following detailed description of the various embodiments having reference to the attached figures, the subject matter described herein not being limited to any particular preferred embodiment(s) disclosed.

BRIEF DESCRIPTION OF THE DRAWINGS

FIGS. 4A-4E show various views of the device shown in FIG. 1A, and more particularly, show the same-side retractable deployment relationship of a scalpel and a tissue spreader along a common slider track in accordance with one embodiment (FIG. 4E), and an opposite side retractable deployment relationship of a scalpel and a tissue spreader along a common slider track in accordance with another embodiment (FIG. 4D).

FIGS. 8A-8E show top, side, side with "Quick Trach" cartridge inserted and withdrawn from a housing, back, and front views, respectively of an alternative embodiment of a device in accordance with an embodiment.

FIGS. 9A-9L show various views of one embodiment having a removably attached combination tracheal "hook" and tissue-spreader tool.

FIGS. 15A-15E show an apparatus for providing a passage into the body in accordance with still another embodiment.

DETAILED DESCRIPTION

Figure 1A:
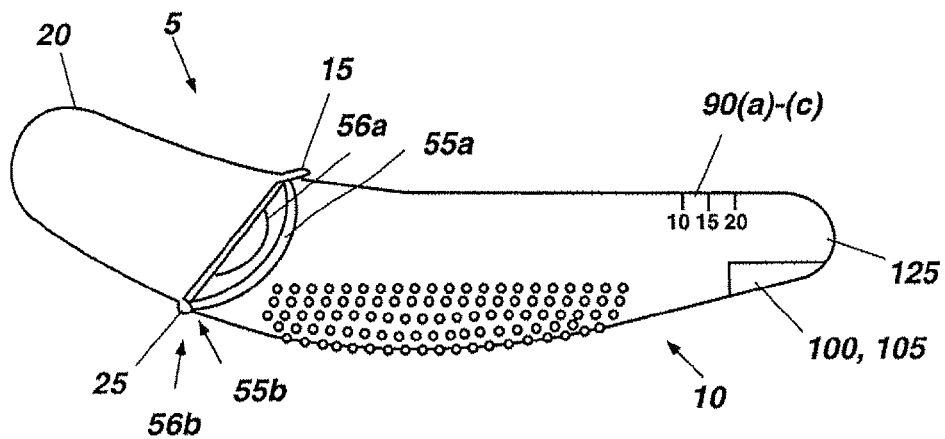
FIG. 1A shows one embodiment of a durable, compact, lightweight, ergonomic hand-held device having universal and common components and methodology of execution for use in, among other things, one-hand operation in providing an opening into the body such as in establishing an airway in medical procedures including tracheostomies and cricothyroidectomies.

Embodiments of the invention will now be described with references to the accompanying Figures, wherein like reference numerals refer to like elements throughout. The terminology used in the description presented herein is not intended to be interpreted in any limited or restrictive manner, simply because it is being utilized in conjunction with a detailed description of certain embodiments. Furthermore, various embodiments (whether or not specifically described herein) may include novel features, no single one of which is solely responsible for its desirable attributes or which is essential to practicing the subject matter herein described.

As used herein the terms tracheotomy and cricothyroidotomy, and any form of each word, are considered to be interchangeable for purposes of explaining the subject matter provided herein.

Generally, in one embodiment, the device described herein provides for a compact universal cricothyrotomy (CRIC) kit that is relatively safer, more efficient, consistent, and easier to use when executing or providing an opening into the body, such as when performing an emergency tracheotomy, in all environments, including dark and "hot" combat theater situations, when compared to known emergency tracheotomy devices.

The device provides, among other things, (1) visible and infra-red light sources, (2) a combination of a clean retractable scalpel and a tissue spreader device, (3) incision depth gauging and regulation, (4) tissue preparation and administration components, (5) a standard (6 mm) endotracheal tube, and (6) tube stabilization device all integrated into a durable, compact, lightweight, ergonomic hand-held device for one-hand operation in establishing an airway.

FIG. 1A shows a side view of one embodiment of the device or CRIC kit 5. As shown in the figure, this embodiment of the device 5 includes a curved ergonomically shaped housing 10 designed to fit in the palm of a person's hand. In one embodiment, the housing 10 is constructed from molded plastic such as a polycarbonate, polypropylene, etc. The further use of other plastics, as well as other materials such as metals, composites, glass, rubber, and the like, in the construction of the device will depend on a number of factors including, for example, material cost, durability, and the intended use of a part.

Figure 2A:
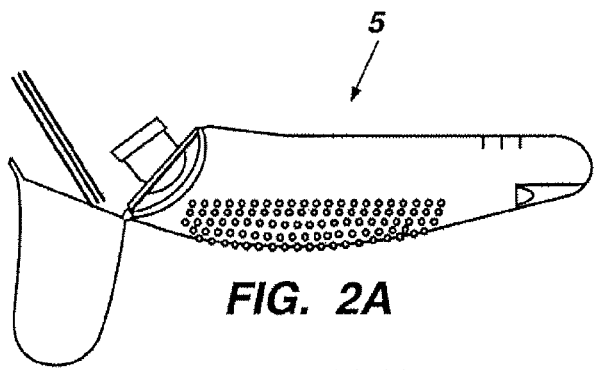
FIGS. 2A-2F illustrate one method of performing or executing an emergency tracheotomy (cricothyroidectomy) utilizing the device described herein.

Among other things, the housing 10 includes a flip tab 15 positioned to rotatably open a storage hatch 20 about a rotatable hinge 25 for accessing a storage compartment 30 for retention of tissue preparation components such as prep-wipes 40, retainer strap 35 for endotracheal tube stabilization, and access to a standard 6 mm endotracheal breathing tube 45 (see also FIGS. 2A-2F) that are positioned within a tube cavity 50 formed within the housing 10. When the storage hatch 20 is in the open position (FIG. 2A) cuff retainers 55(a), 55(b) having retainer strap slits 56(a), 56(b) positioned on opposite sides of the enodtracheal tube 45 are available to assist the user in removing the endotracheal tube 45 from the tube cavity 50. When the storage hatch 20 is in the closed position (FIG. 2B) the cuff retainers 55(a), 55(b) extend outside of the housing 10.

Figure 1B:
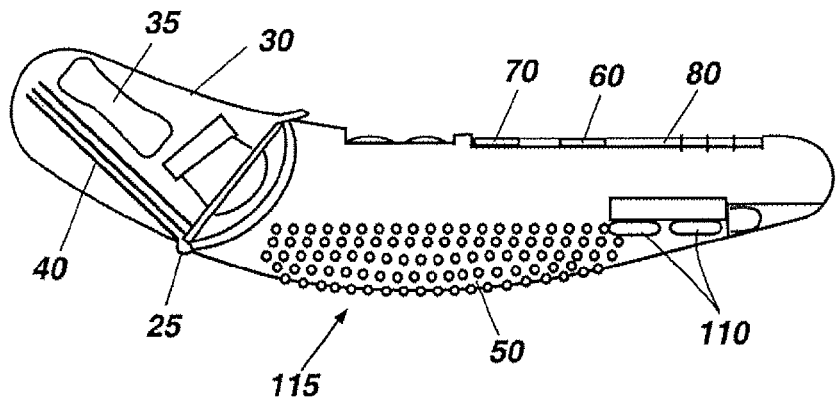
FIGS. 1B-1C show cutaway views of the apparatus shown in FIG. 1A.
Figure 1C:
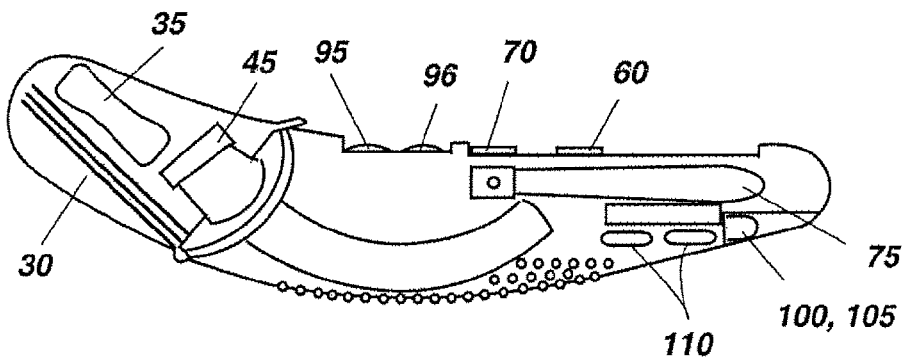

As shown in FIG. 1B and FIG. 1C, the housing 20 further includes a first slider switch 60 for extending and retracting a scalpel 65 (FIG. 2C), and a second slider switch 70 for extending and retracting a tissue spreader 75. In this regard, the scalpel 65 and tissue spreader 75 are operably connected to respective slider switches 60, 70 by well-known means such as those methods used to extend and retract the blade of a box cutter.

In a retracted position the scalpel 65 and tissue spreader 75 are disposed or stored safely and conveniently within housing 10. The first slider switch 60 and second slider switch 70 are positioned within a slider track 80 for extending and retracting the scalpel 65 and tissue spreader 75 away from the housing 10 and toward the housing 10. In other words, in one embodiment, the device described herein provides for retractable deployment of a scalpel 65 and a tissue spreader 75 along a common slider track 80.

In the embodiment shown in FIGS. 1A-1C, the first or scalpel slider switch 60 is positioned forward of the second or tissue spreader slider switch 70 within the slider track 80 for retractable deployment from the same side of the device 5.

Figure 4D:
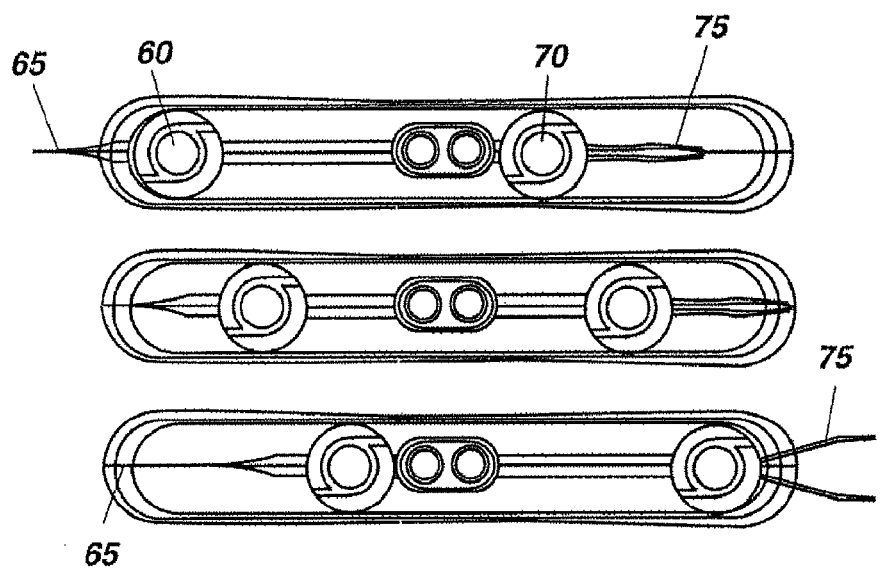

In an alternative embodiment shown in FIG. 4D, the first or scalpel slider switch 60 is positioned to retractably deploy from one end of the device 5 while the second or tissue spreader slider switch 70 is positioned to retractably deploy from the opposite end of the device 5. Likewise, in this embodiment a single slider track 80 or dual slider tracks (not shown) may be utilized for retractable deployment of the first switch 60 and second switch 70.

Figure 5A:
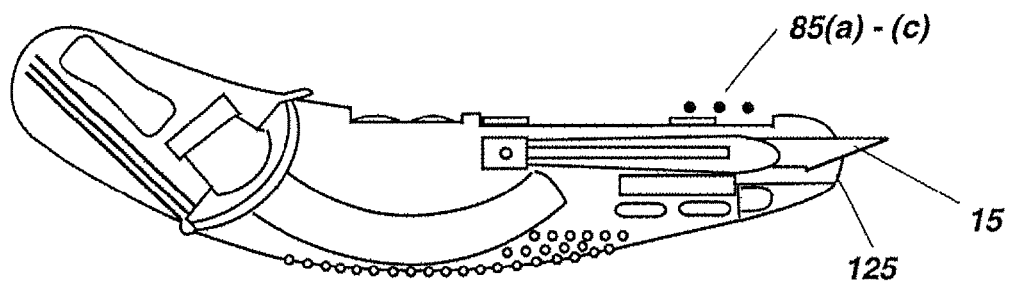
FIGS. 5A-5B show movement of the slider switch and corresponding tissue spreader switch along the slider track to an extension depth of 10 mm.

The slider track 80 may include a plurality of detents 85(a)-(c) positioned at prescribed intervals to provide incision-deep regulation, gauging, and feedback to the user as to the extended or retracted distance of the scalpel 65 (see FIG. 5A). Scalpel distance demarcations 90(a)-(c) may also be provided for incision-depth regulation and gauging by visual verification and confirmation of the scalpel 65 extension or retraction distance. In one example, verification of scalpel distance positioning is provided by markings such as 10, 15, and 20 millimeters molded directly into the housing 10. These markings 90(a)-(c) confirm the scalpel positioning as provided by the detents 85(a)-(c) on the associated slider track 80.

Figure 6A:
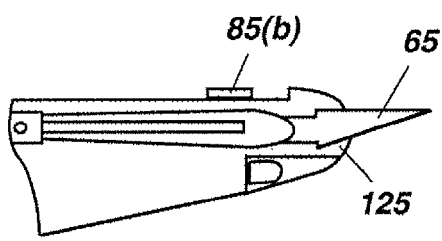
FIGS. 6A-6B are similar to FIGS. 5A-5B and show movement of the slider switch and corresponding tissue spreader switch along the slider track to an extension depth of 15 mm.
Figure 7A:
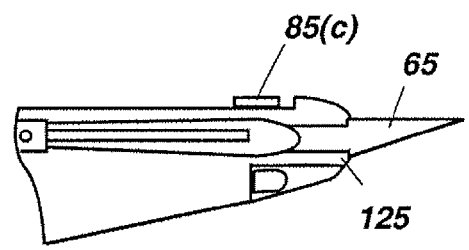
FIGS. 7A-7B show movement of the slider switch and corresponding tissue spreader switch along the slider track to an extension depth of 20 mm.

Accordingly, as shown in FIGS. 5A, 6A, and 7A, as the scalpel switch 60 is moved from left to right in each of the figures from a first detent position 85(a) to a second and a third detent position 85(b), 85(c), the scalpel 65 is moved outward from the housing 10 approximately 10 mm, 15 mm, and 20 mm.

As further shown in FIG. 1C, the housing 10 also provides for switch and/or pushbutton 95, 96 activation and verification of IR (infrared) and visible light spectrum LEDs 100, 105 mounted on the front-underside of the housing 10. Lithium ion batteries 110 are housed within the housing 10 to provide power to the LEDs 100, 105. "Gripper nubs" (raised bumps) 115 may be molded into the housing 10 or formed from rubber and applied to the housing 10 to provide a textured surface to assist the user in holding, gripping, or otherwise maneuvering the device 5.

Figure 2B:
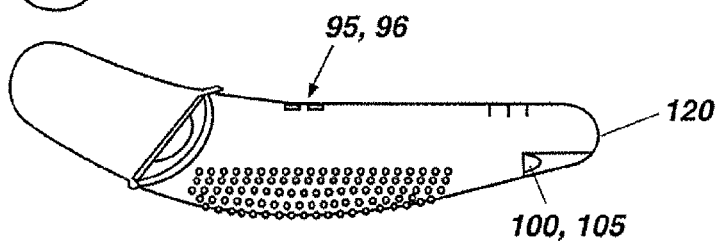
Figure 2C:
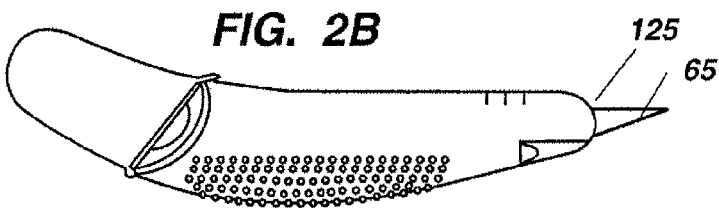

As shown in FIGS. 2A-2F, the device 5 is a relatively simple, safe, and easy to use device. In one method, use of the device 5 to establish an airway in medical procedures, including tracheostomies and cricothyrotomies, begins by opening the storage hatch 20, removing one or more prep-wipes/pads 40, and wiping the intended site or area of incision 120 for establishment of an airway. As shown in FIG. 2B, the storage hatch 20 is closed and depending on the lighting conditions either the IR LED light 100 or visible-spectrum LED light 105 may be activated by the associated single pushbutton membrane or switch 95, 96 to illuminate the site of incision 120. As shown in FIG. 2C, establishing an airway then proceeds by deploying or extending the scalpel 65 a predetermined distance (10 mm, 15 mm, or 20 mm) as indicated by the scalpel demarcations 90(a)-(c) and/or the detents 85(a)-(c).

In this regard, in the embodiment shown in FIGS. 4A-4C, and 4E, the device 5 provides for safe extension and retraction (deployment) of the scalpel 65 by a half-circle slider switch 60 moved along a slider track 80 having detents 85(a)-(c) position to indicate the scalpel 65 extension and retraction distances of 10 mm, 15 mm, and 20 mm from the housing 10, as well as the extension and retraction of an associated tissue spreader 70 by a corresponding half-circle slider switch 70.

Figure 3:
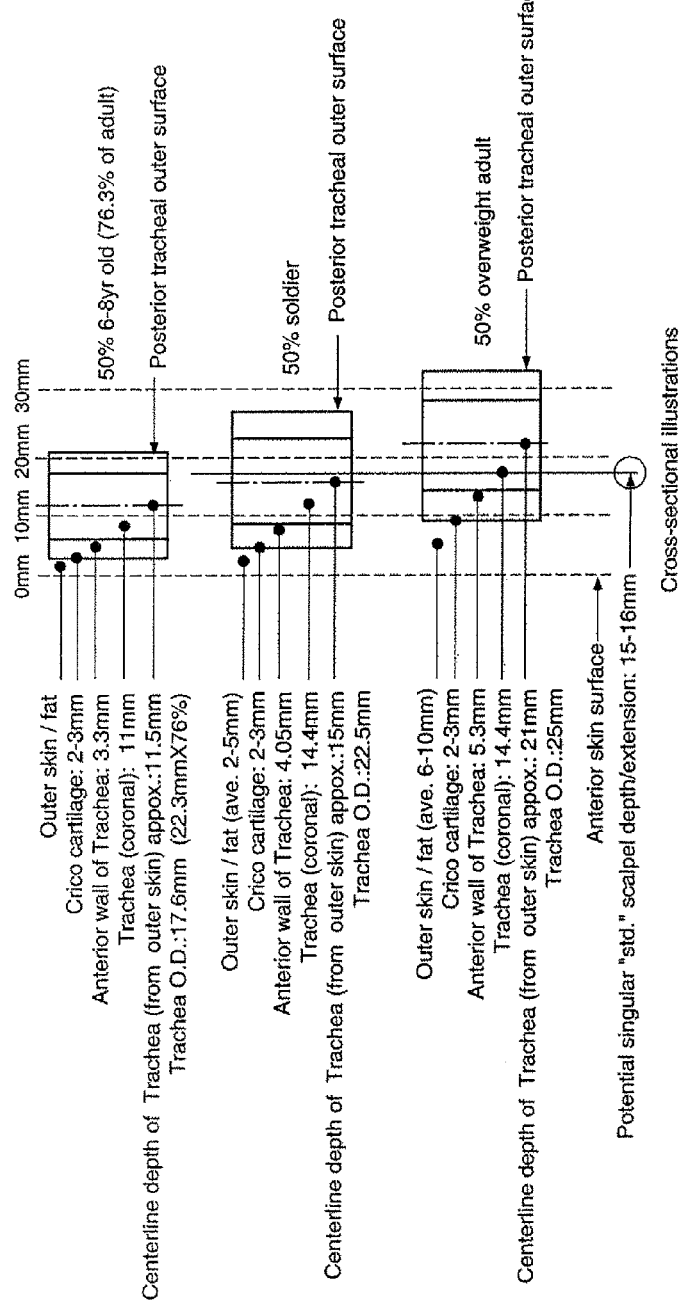
FIG. 3 shows tracheal and associated tissue depths for selected persons, and proposed scalpel depth information for retractable deployment of the scalpel.

As shown in FIG. 3, the 10, 15, and 20 millimeter depth of the scalpel 65 is generally shown as approximating the centerline depth of the trachea for 50% of certain individuals. For example, persons 6-8 years old generally require an incision depth of 10 mm, soldiers a depth of 15 mm, and overweight adults a depth of 20 mm. Accordingly, once the patient has been assessed for size and categorized as to trachea centerline depth, extension of the scalpel 65 to the appropriate depth ensures adequate penetration through the outer skin (epidermis), cricocartilage, and anterior wall of the trachea, while preventing too-deep penetration of the scalpel 65 that could potentially cause damage to the posterior tracheal inner surface. In regard to scalpel 65 extension, the front of the housing 125 (i.e., the part of the housing directed toward the site of incision) acts as a buffer or barrier to prevent further movement of the scalpel 65 into the trachea cavity that may result in excessive penetration of the scalpel 65 beyond the selected penetration/extension depth 85(a)-(c), which results in damage to the trachea wall and/or other vital areas such as the esophagus. Persons of ordinary skill in the art will understand that other scalpel depths may replace and/or supplement those indicated above.

Figure 2D:
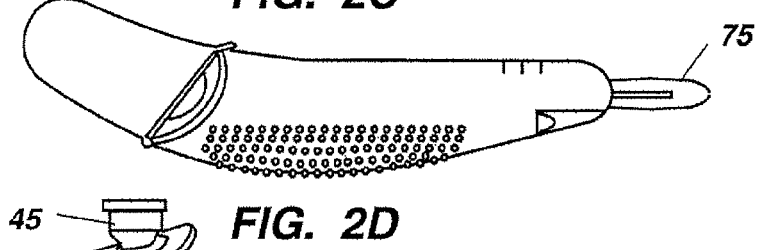
Figure 4E:
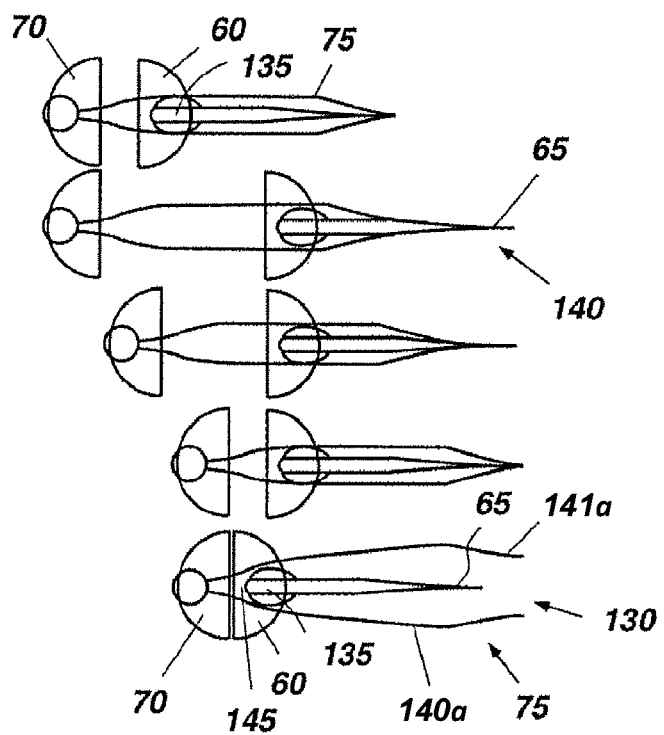
Figure 5B:
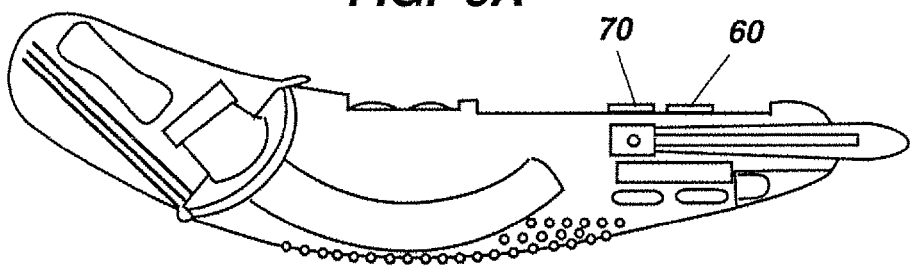
Figure 6B:
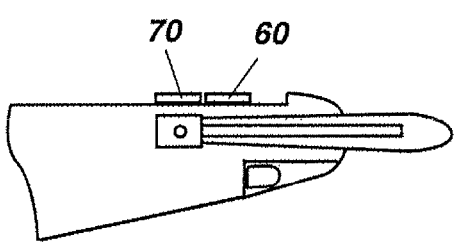
Figure 7B:
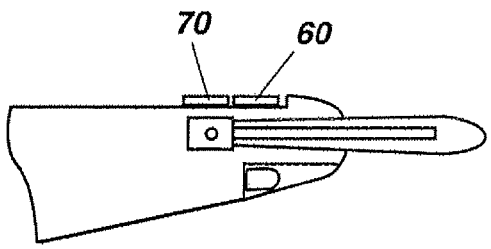

As shown in FIG. 2D, and more specifically in the sequence of illustration shown in FIG. 4E, after an incision is made with the scalpel 65, the tissue spreader 75 is extended forward along the slider track 80 using a half-circle slider switch 70 similar to the half-circle slider switch 60 used to extend the scalpel 65 forward. In this regard, the half-circle tissue spreader slider switch 70 is brought forward to mate with the half-circle scalpel slider switch 60. Mating of the tissue spreader switch 75 with the scalpel switch 60, is further shown in FIGS. 5B, 6B, and 7B at 10 mm, 15 mm, and 20 mm, respectively along the slider track 80.

Movement of the tissue spreader slider switch 70 along the slider track 80 until it mates with the scalpel slider switch 60 permits a bifurcated tapered leading end 130 of the tissue spreader 75 to: (1) slide forward in a "closed" position "hugging" the scalpel 65, (2) to eventually penetrate into the tracheal cavity through the incision created by the scalpel 65, and (3) to move from the "closed" position to an "open" position to spread the incision to an approximate distance of 1.27 centimeter (0.5") to allow room for insertion of the breathing tube 45. Persons of ordinary skill in the art will understand that the device 5 may be designed so that the tissue spreading distance may vary from the distance stated above to accommodate other size tubes or similar articles for maintaining an airway.

As further shown in FIG. 4E, opening or spreading of the scalpel's bifurcated leading edge 130 is facilitated by the enlarged distal end 135 (i.e., that end of scalpel opposite the cutting end 140) of the scalpel 65 positioned between a first arm 140a and a second arm 141a of the tissue spreader 75. In this regard, as the tissue spreader 75 is moved forward along the slider track 80 the enlarged distal end 135 of scalpel 75 forces the tapered trailing end 145 of the tissue spreader 75 apart, resulting in a similar spreading apart of the leading end 130 of the tissue spreader 75. Mating of the tissue spreader switch 70 with the scalpel switch 60 acts to regulate and correspond the depth of tissue spreader 75 penetration into the incision opening with the depth of scalpel 65 penetration into the incision opening. As shown in FIG. 4E, retractable deployment distance of the tissue spreader 75 is such that the tissue spreader 75 extends beyond the retractable deployment distance of scalpel 65 to permit insertion of the endotracheal breathing tube 45 into the incision site without removal of the tissue spreader 75 from the incision.

Figure 2E:
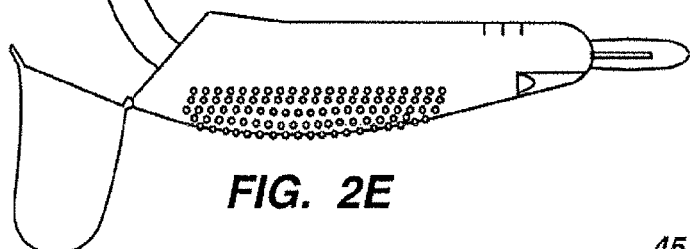
Figure 2F:
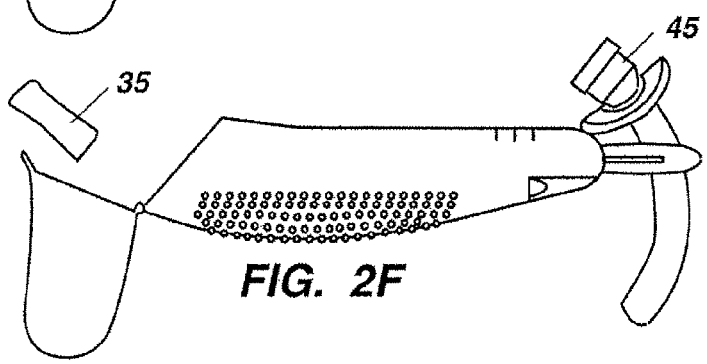

As shown in FIG. 2E and FIG. 2F, once the incision is spread open to a diameter of approximately 1.27 cm by the tissue spreader 75, the endotracheal tube 45 and endotracheal tube retainer or tie-down strap 35 are removed from the storage compartment 30. The endotracheal tube 45 is then inserted between the bifurcated leading end 130 of the tissue spreader 75 and into the incision opening. The device 5 (including the tissue spreader 75) is retracted or removed from the incision, and the endotracheal tube retainer strap 35 is attached to endotracheal tube 45 along the cuff retainer slits 56(a)-(b) and tied around the patient's neck to secure the endotracheal tube 45 in place.

An alternative embodiment of the device 5 is shown in FIGS. 8A-8E. In this embodiment, the device 145 includes a reusable housing 150 with a butterfly-opening latch 147, and a slidable cartridge housing 146 that moves and deploys the inserted disposable/replaceable pro-trach cartridge 155 temporarily retained therein for storage and deployment in establishing an airway. The cartridge 155 includes a combination piercing tube 156 surrounded by a sleeve 157. A storage compartment 160 is provided to retain an industry standard 12 mm breathing tube adaptor 170. The breathing tube adapter 170 is attached to the sleeve 157 to maintain establishment of the airway. Accordingly, one method of establishing an airway using the device shown in FIGS. 8A-8E includes, bringing the piercing tube 156 and associated sleeve 157 forward by slide switch 158, 159 activation to the site of intended incision, making an incision using the piercing tube 156, and inserting the sleeve 157 into the site of incision by the continued forward movement of the combination piercing tube 156 and sleeve 157.

After insertion of the sleeve 157 into the incision site, the sleeve 157 and piercing tube 156 are released from the housing 150 by the butterfly latch 147 to remain disposed within the incision site. In this regard, the housing 150 is made available for accepting another similarly constructed pro-trach cartridge 155 therein for use in establishing an airway. The 12 mm breathing tube adaptor 170 is then removed from the storage compartment 160, attached to the sleeve 157 by threading, friction fit, or a similar attachment means, and retained in place to maintain establishment of the airway.

As shown in FIGS. 9A-9L, the device 5 may further include a removably attached combination tracheal "hook" and tissue-spreader tool 200. The combination tool 200 is of a general durable, sterilizable, single-piece injection molded, translucent polycarbonate material construction. Although the length of the combination tool 200 may vary, a combination tool 200 length of approximately 4.5 inches is typically adequate for most applications. The shape of combination tool 200 corresponds to the shape of the housing 10 so that when placed in a closed or retracted position (explained below) the tool 200 stores directly onto the CRIC housing 10.

As shown in at least FIGS. 9C-9F, the combination tool 200 includes a first end 201 having a "hook" shaped tip 202, and a bifurcated second end 203 (opposite the first end 201) having a first leg 204A and a second leg 204B biased in a normally open position. The combination tool 200 further includes a first extension 205A positioned on one leg 204A of the bifurcated end 203, and a second extension 205B positioned on the other leg 204B of the bifurcated end 203. As shown in comparing FIG. 9C to FIG. 9F, the shape of the first extension 205A and second extension 205B may vary to facilitate compression or closing of the bifurcated second end 203.

Furthermore, a dual-purpose first stem 206A is positioned at the tip of one leg 204A and a dual-purpose second stem 206B is positioned at the tip of the other leg 204B. Each extension 205A, 205B, and each stem 206A, 206B extend laterally from the combination tool 200. As further shown in comparing FIG. 9C to FIG. 9F, the shape of the first stem 206A and second stem 206B may likewise vary to facilitate the necessary spreading of tissue as intended by the bifurcated second end 203. In this regard, in one embodiment, the opening between the legs 204A, 204B of the bifurcated end 203 of the combination tool 200 in a relaxed state (shown in FIG. 9F) has an inside diameter of approximately 0.625 inches and an outside diameter of approximately 0.75 inches. Further in this regard, in one embodiment, the opening between the legs 204A, 204B of the bifurcated end 203 of the combination tool 200 in a compressed state (shown in Figure H) is approximately 0.13 inches.

In one embodiment, protrusions 210A, 210B having locating holes positioned 211A, 211B therein are molded into the housing 10 of the device 5 for removably receiving an associated stem 206A, 206B so as to rotatably retain the combination tool 200 onto the housing 10. In this regard, force applied in the direction of arrows "A" (FIG. 9C) to the first and second extensions 205A, 205B, typically by squeezing or flexing the extensions toward each other, brings together the first and second stems 206A, 206B. The stems 206A, 206B are then positioned between the protrusions 210A, 210B so that the stems 206A, 206B lineup with the locating holes 211A, 211B. Force applied to the first and second extensions 205A, 205B is then removed causing the bifurcated second end 203 to move in the direction of arrow "B" (FIG. 9C), biasing the second end 203 to the open position, and permitting the stems 206A, 206B to be removably received into the locating holes 211A, 211B.

Figures 9A, 9B, 9C, 9D:
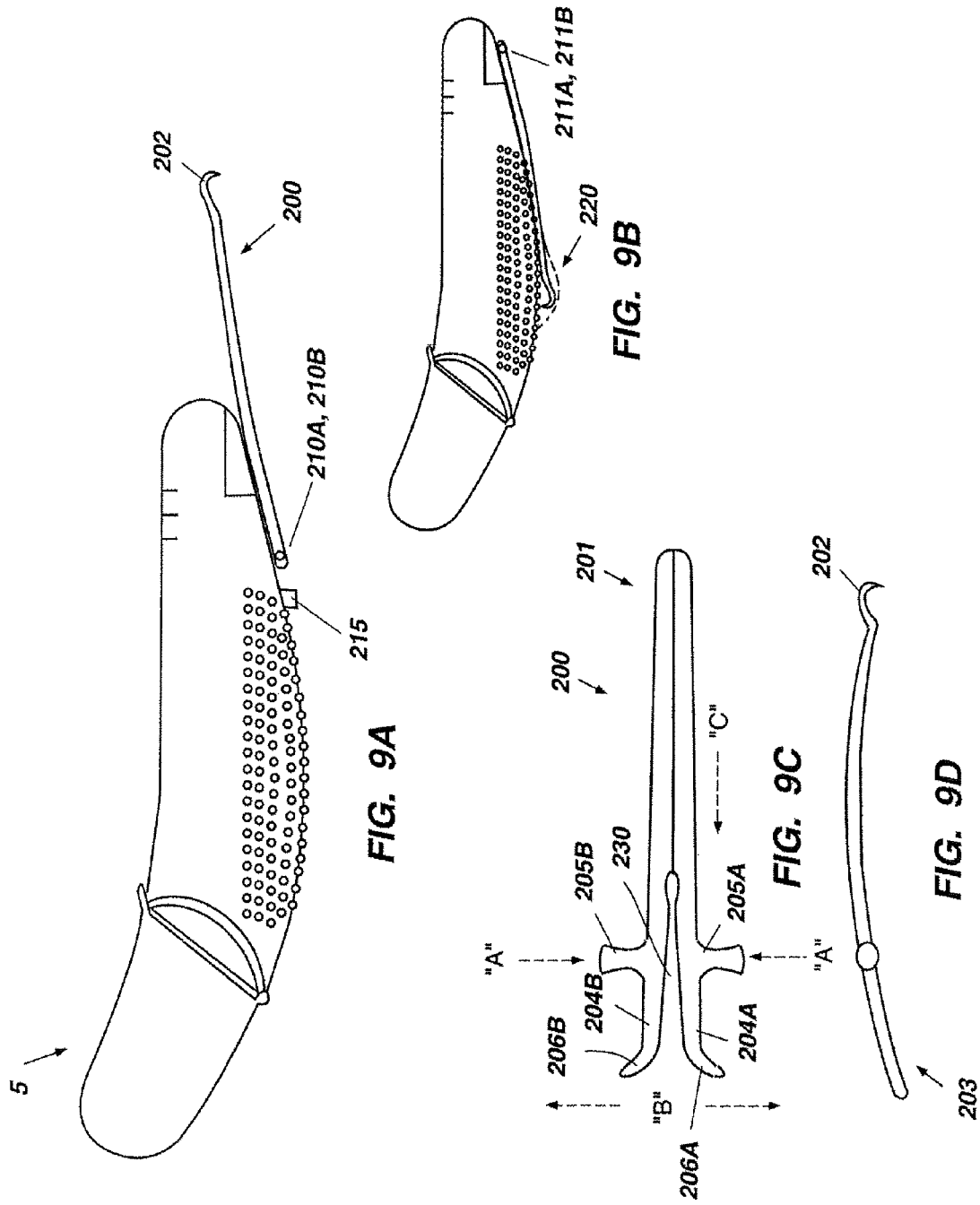

Once the first and second lateral stems 206A, 206B are positioned inside the locating holes 211A, 211B, the combination tool 200 is capable of being rotated approximately 180 degrees from a closed or retracted position (FIG. 9A) to an open or extended position (FIG. 9B). Preferably, a retaining clip 215 having detents (not shown) formed therein is molded into the housing 10 to further assist in retaining the combination tool 200 by holding, gripping, or otherwise securing the first end 201 of combination tool 200 while in the closed position. In one embodiment, the housing 10 is molded to include a "sheath" like storage extension 220 for protecting the "hook" shaped tool 202 during storage of the combination tool 200. In this regard, the "sheath" like extension 220 may be constructed to include the retaining clip 215 mention above, or a trough of reduced width may be included to frictionally secure the first end 201 of the combination tool 200.

In practice, the combination device 200 may remain attached to the housing 10 and rotated into the extended position so that the "hook" shaped tip 202 of the first end 201 may be inserted into a previously made incision in the tissue. The tissue may then be distended by moving the device 5 with attached "hook" in direction "C" (FIG. 9C) so the incision and/or tissue may be irrigated, for example.

Alternatively, as detailed above, the combination device 200 may be removed from the housing 10 and used independently as a stand alone tool or in conjunction with the various design features of the device 5 explained above. In this regard, the lateral stems 206A, 206B of the bifurcated second end 203, previously used to rotatably retain the combination device 200 to the housing 10, are made available for insertion into an incision. Preferably, when biased to the open position, the bifurcated second end 203 spreads the tissue apart a minimum of 6 mm to accommodate a standard size endotracheal tube 45 or similar device.

Variations of the combination tool shown in at least FIGS. 9C and 9F include modifications to the length and shape of the space or opening 230 extending between the opposite legs 204A, 204B of the bifurcated end 203 to facilitate spreading of the legs or tines 204A, 204B, as well as the addition of integrated thumb/finger recesses 235A, 235B along the sides of the combination tool 200.

Figure 10A:
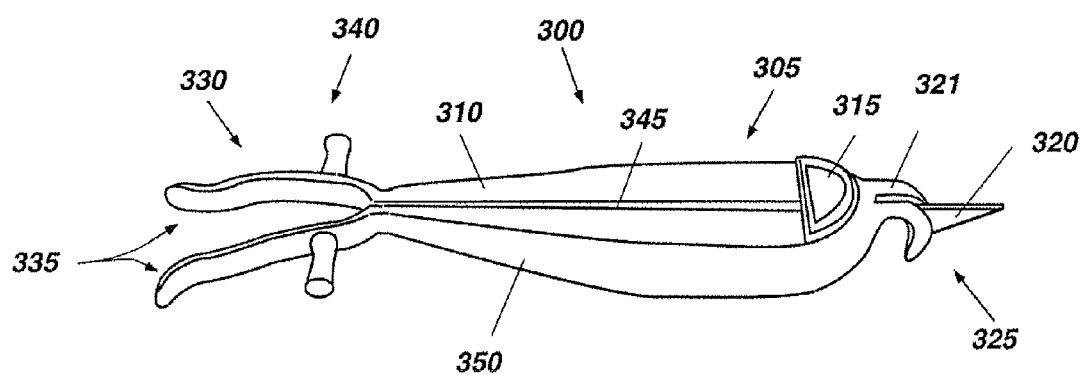
FIGS. 10A and 10B shows a general-purpose tool for providing a passage into the body in accordance with one embodiment.
Figure 10B:
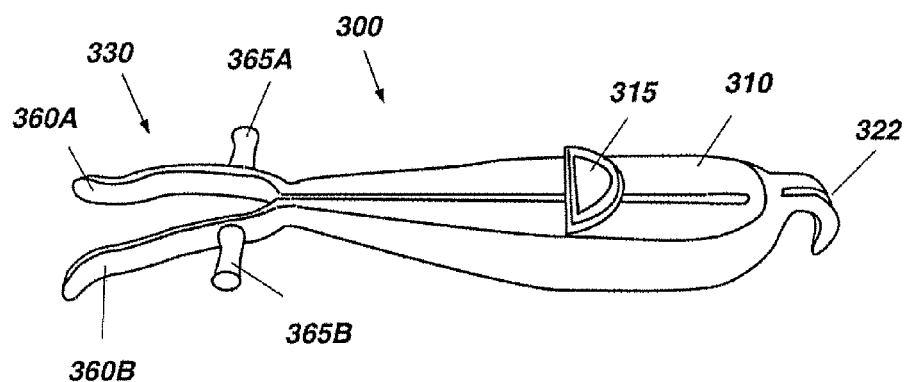

In still another embodiment, as shown in FIGS. 10A and 10B, the device may be embodied in the form of a general-purpose tool 300 for providing a passage into the body. In this regard, the tool 300 includes a tool body 305, preferably of a one-piece molded construction, having an elongated slider track 310 formed therein.

The tool 300 preferably further includes a slider switch 315 movably disposed within the slider track 310 for extending and retracting a scalpel 320 from a first side 325 of the tool body 305. In the retracted position the scalpel 320 is housed between opposite sides 345, 350 of the tool body 305. In this regard, with the scalpel 320 in the retracted position the tool body 305 may be "safely" handled, carried, or otherwise manipulated as the scalpel 320 is stored within the tool body 305. In this embodiment, the tool body 305 may be constructed of a semi-translucent material, such as plastic, to provide visual assessment of the scalpel 320 position as well as the tissue area of the patient.

As shown in FIG. 10A, the tool body 305 further includes a "hook" shaped protrusion 321 extending from the same side 325 of the tool body 305 as the scalpel 320 when the scalpel 320 is in an extended position. The extension 321 includes an elongated slit 322 (FIG. 10B) generally located in the center of the "hooked" protrusion 321 for receiving the scalpel 320 therethrough when the scalpel 320 is extended from the tool body 305. The protrusion 321 functions as a depth guard for the scalpel 320 when making a tissue incision, and as a "hook" 321 for tissue displacement when the scalpel 320 is retracted. In this regard, typical scalpel 320 extension from the protrusion 321 is generally limited to less than 16 mm.

A tissue spreader 330 having a bifurcated end 335 may be included and located on a second or opposite side 340 of the tool body 305. The bifurcated end 335 includes a first leg 360A and a second leg 360B biased in an open position. The tool 300 further includes a first extension 365A positioned on one leg 360A of the bifurcated end 335, and a second extension 365B positioned on the other leg 360B of the bifurcated end 335.

Accordingly, in practice, use of the tool 300 shown in FIG. 10A and FIG. 10B, at least with respect to the "hook" shaped protrusion 321 and the bifurcated tissue spreader 330 is substantially similar to use of the combination tool 200 shown in FIGS. 9A-9D above. However, as the tool 300 shown in at least FIGS. 10A and 10B further includes a retractable scalpel 320, the tool 300 may generally be considered an all or multi-purpose tool for providing a passage into the body.

Figure 11A:
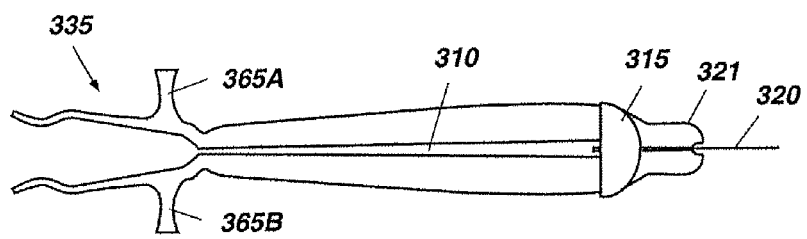
FIG. 11A is top view of the tool of the tool shown in FIGS. 10A and 10B showing a scalpel extended between an elongated slit formed in the "hooked" protrusion.
Figure 11B:
FIG. 11B and FIG. 11C respectively show side views of the tool with the scalpel in an extended and retracted position.
Figure 11D:
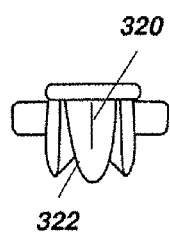
FIG. 11D shows a front view of the tool including a first extension and a second extension of a bifurcated end, the "hooked" protrusion with its elongated slit, and the scalpel.
Figure 11C:
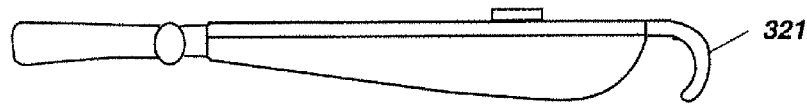
Figure 11E:
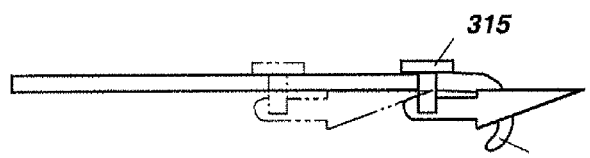
FIG. 11E shows a side view of the tool with the sides of the tool body removed to show the connection between the slider switch and the scalpel.
Figure 11F:
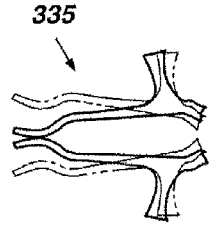
FIG. 11F shows the bifurcated end of the tool and illustrates a general range of motion of the tissue spreader.

Other figures, including FIGS. 11A-11G, show various views of the multi-purpose tool 300 described above. Specifically, FIG. 11A is top view of the tool 300 showing the scalpel 320 extended between the elongated slit 322 formed in the "hooked" protrusion 321. Side views of the tool 300 with the scalpel 320 in an extended and a retracted position are shown in FIG. 11B and FIG. 11C, respectively. FIG. 11D, shows a front view of the tool 300 including the first extension 365A and a second extension 365B of the bifurcated end 335, the "hooked" protrusion 321 with its elongated slit 322, and the scalpel 320. FIG. 11E, is a side view of the tool 300 with the sides 345, 350 of the tool body 305 removed to show the connection between the slider switch 315 and the scalpel 320. FIG. 11F shows the bifurcated end 335 of the tool 300 and illustrates a general range of motion of the tissue spreader 330.

A further embodiment of a general-purpose tool 400 for providing a passage into the body is shown in FIGS. 12A-12E. In this regard, many of the design features found in the multi-purpose tool 300 shown in at least FIG. 10A and FIG. 10B, including a tool body 405, a slider track 410 formed therein, and a slider switch 415 disposed within the slider track 410 for extending and retracting a scalpel 420 from a first side 425 of the tool body 405. However, in contrast to the previously mentioned all-purpose tool 300, this embodiment of the tool 400 includes a depth guard/"hook"/tissue spreader combination 430 integrated into a single device on the same side 425 of the tool body 405 as the scalpel 420 when extended from the tool body 405.

Figure 12A:
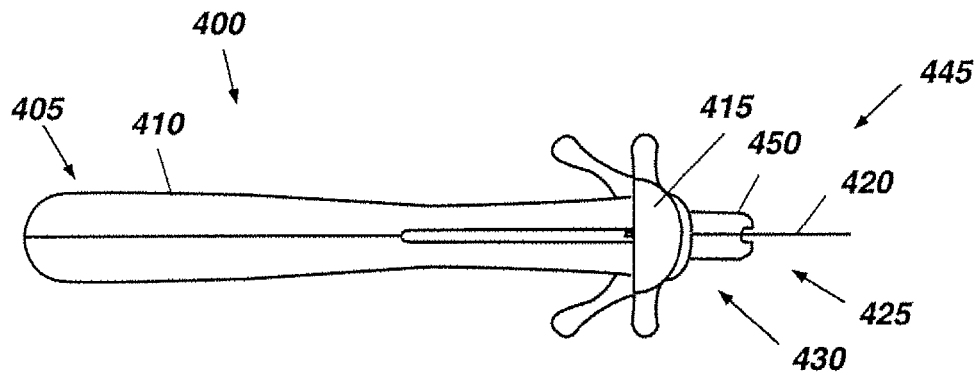
FIGS. 12A-12E show an apparatus for providing a passage into the body in accordance with another embodiment.
Figure 12B:
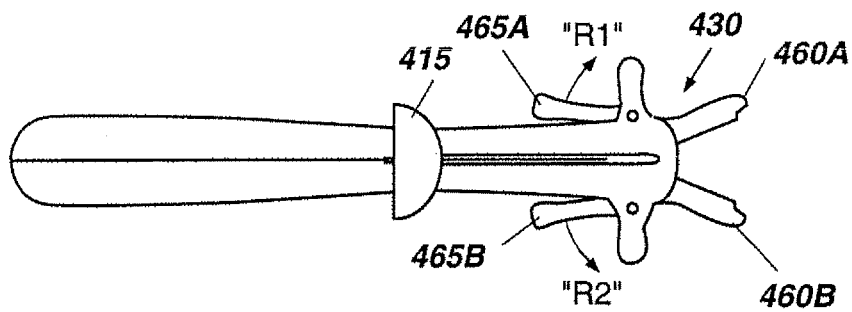
Figure 12C:
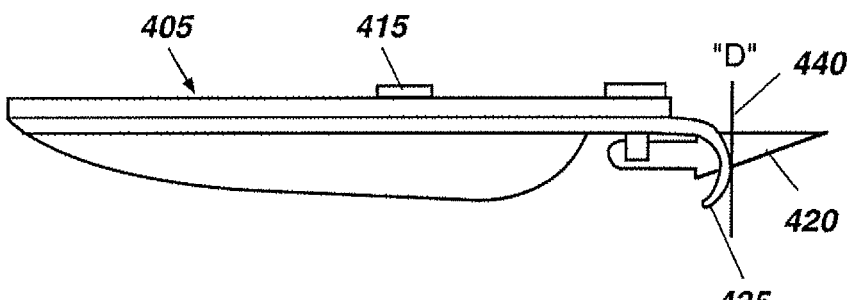

Accordingly, the integrated device 430 combines a tissue "hook" 435, incision depth guard 440 (provided by the front face of the tissue hook 435, tissue hook 440), and tissue spreader 445 having a bifurcated end 450. Preferably, the bifurcated end 450 includes a first leg 460A and a second leg 460B generally biased in a closed position (FIG. 12A), and a first rotatable arm 465A connected to the first leg 460A and second rotatable arm 465B connected to the second leg 460B for rotatably positioning the first and second legs 460A, 460B of the tissue spreader 445 in an open position. In contrast to activation of a tissue spreader 75 by a slider switch 70 (see the tool 5 shown at least in FIG. 4A), activation of the tissue spreader device of FIG. 12B is provided by the rotatable arms 465A, 465B connected to a corresponding tissue spreader leg 460A, 460B and rotating along rotation paths designated as "R1" and "R2" in FIG. 12B. In this regard, rotation of each rotatable arm 465A, 465B toward the tool body 405 opens or spreads the first leg 460A and second leg 460B of the bifurcated end 450 while rotation of each rotatable arm 465A, 465B away from the tool body 405 closes or brings together the first leg 460A and the second leg 460B of the bifurcated end 450.

Figure 12D:
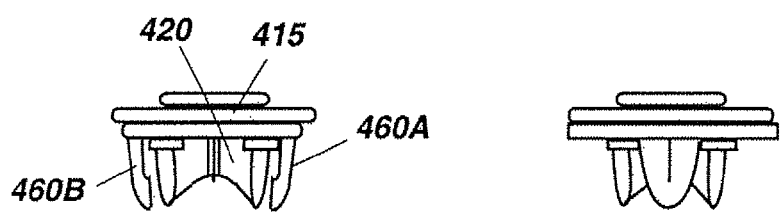
Figure 12E:
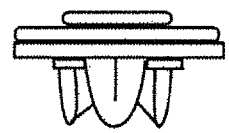

Accordingly, the combination device 430 allows the scalpel 420 to pass between the legs 460A, 460B of the tissue spreader 445 to permit an incision to be made in a patient (FIG. 12D and FIG. 12E). The incision depth guard 440 maintains a scalpel 420 incision depth of less than 16 mm. Once an incision is made, sequential use of the tissue hook 435 for displacement or distention of the tissue, and tissue spreading utilizing the tissue spreader 445 can take place immediately. Dents 85(a)-(c) such as those explained in conjunction with the tool 5 of at least FIGS. 5A-7B may be provided on the tool body 405 thereby providing for variable extension depths of the scalpel 420 and/or opening distances of the tissue spreader 445. In one embodiment, the maximum distance between the open legs 460A, 460B of the tissue spreader is 19 mm.

Persons of ordinary skill in the art will understand that any distance/measurement discussed within the detailed description, regardless of whether the distance/measurement refers to some aspect of the scalpel, tissue spreader, or hook, is not meant to be an absolute distance/measurement in that the distance/measurement may vary depending on any number of factors, including the device's intended use.

Many of the characteristics relating to the various tools for creating a passage into the body, as described herein, may be adapted in another embodiment of the device such as the device 500 shown in FIGS. 13A-13C and 14A-14D. For example, the device 500 includes a housing 505, a slider track 510 formed therein, and a slider switch 515 disposed within the slider track 510 for extending and retracting a scalpel 520 from a first side 525 of the housing 505.

Figure 13A:
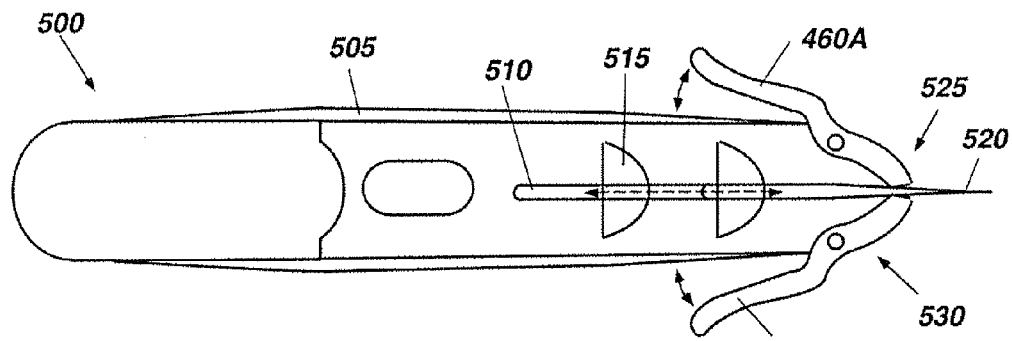
FIGS. 13A-13C and FIGS. 14A-14D show an apparatus for providing a passage into the body in accordance with still another embodiment.
Figure 13B:
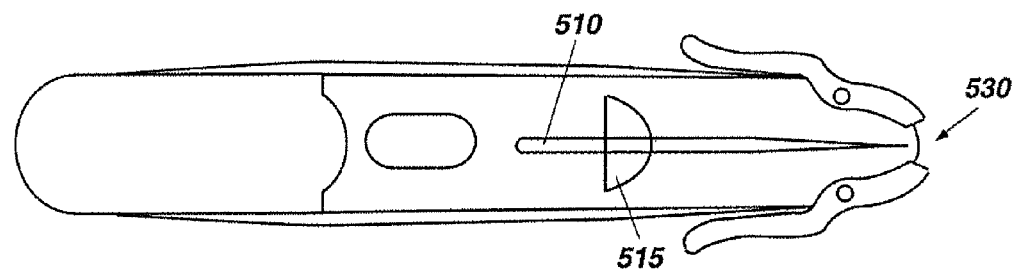
Figure 13C:
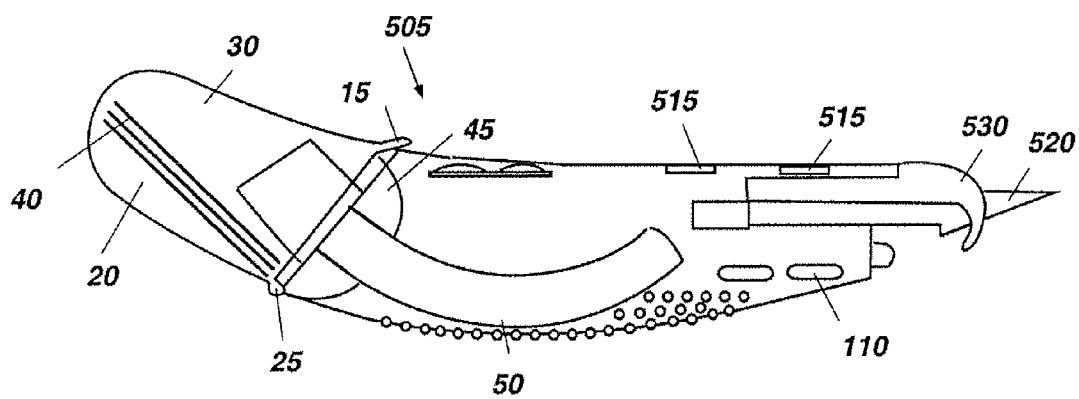

Likewise, the housing 500 shown in FIGS. 13A-13C further includes a bifurcated depth guard/"hook"/tissue spreader combination 530 integrated into a single device on the same side 525 of the housing 505 as the scalpel 520 when extended from the tool body 505. Persons of ordinary skill in the art will understand that structure, mechanics, functionality, and use of the tissue depth guard/"hook"/tissue spreader 530, slider switch 515, and scalpel 520 are substantially the same as those same items shown and explained relative to tool 400 shown in FIGS. 12A-12E. Similar to device 5 shown at least in FIGS. 1A-1C, the housing 505 of the device of FIGS. 13A-13C is curved shaped to ergonomically fit in the palm of a person's hand.

The housing 505 includes a flip tab 15 positioned to rotatably open a storage hatch 20 about a rotatable hinge 25 for accessing a storage compartment 30 for retention of tissue preparation components such as prep-wipes 40, retainer strap 35 for endotracheal tube stabilization, and access to a standard 6 mm endotracheal breathing tube 45 (see also FIGS. 2A-2F) that is positioned within a tube cavity 50 formed within the housing 10. When the storage hatch 20 is in the open position (FIG. 2A) cuff retainers 55(a), 55(b) having retainer strap slits 56(a), 56(b) positioned on opposite sides of the endotracheal tube 45, may be made available to assist the user in removing the endotracheal tube 45 from the tube cavity 50. When the storage hatch 20 is in the closed position (FIG. 2B) the cuff retainers 55(a), 55(b) extend outside of the housing 10.

As shown further in FIGS. 14A-14D, other features of the device 500 may include a plurality of detents 85(a)-(c) positioned at prescribed intervals, scalpel distance demarcations 90(a)-(c) (indicating distances of 5 mm, 10 mm, and 15 mm), pushbutton 95, 96 activation and verification of IR and visible light spectrum LEDs 100, 105 mounted on the front-underside of the housing 505.

Figure 14A:
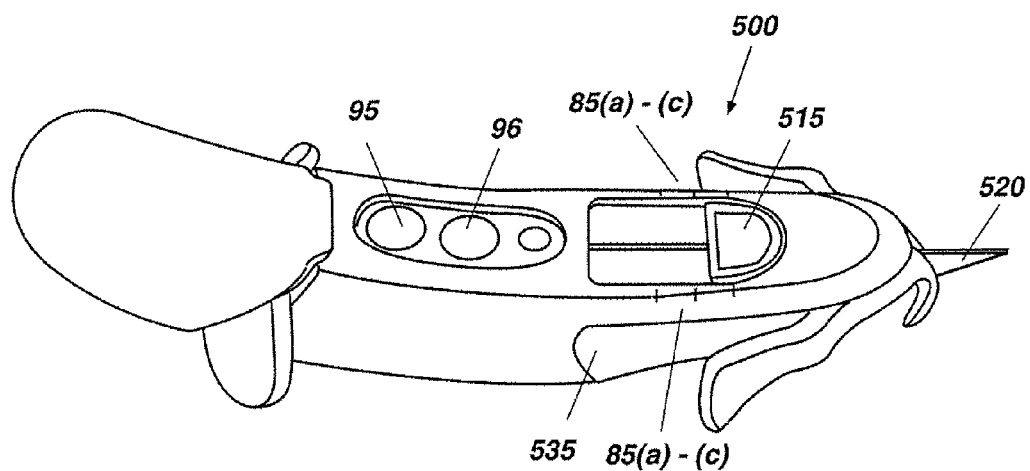
Figure 14B:
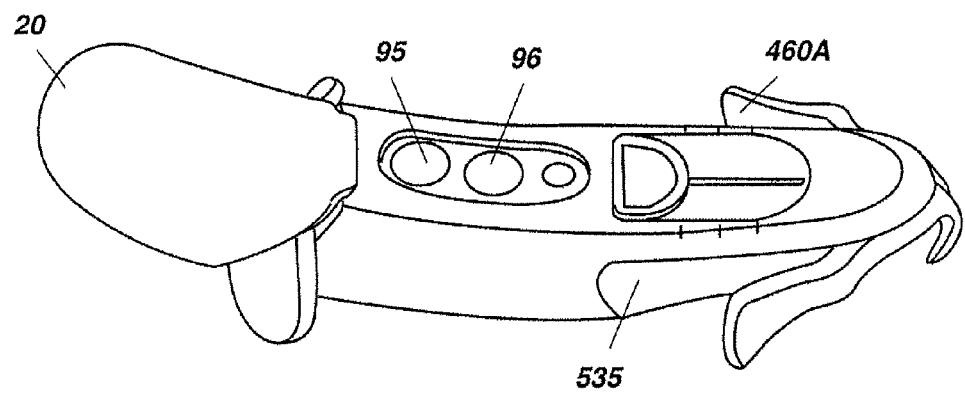
Figure 14C:
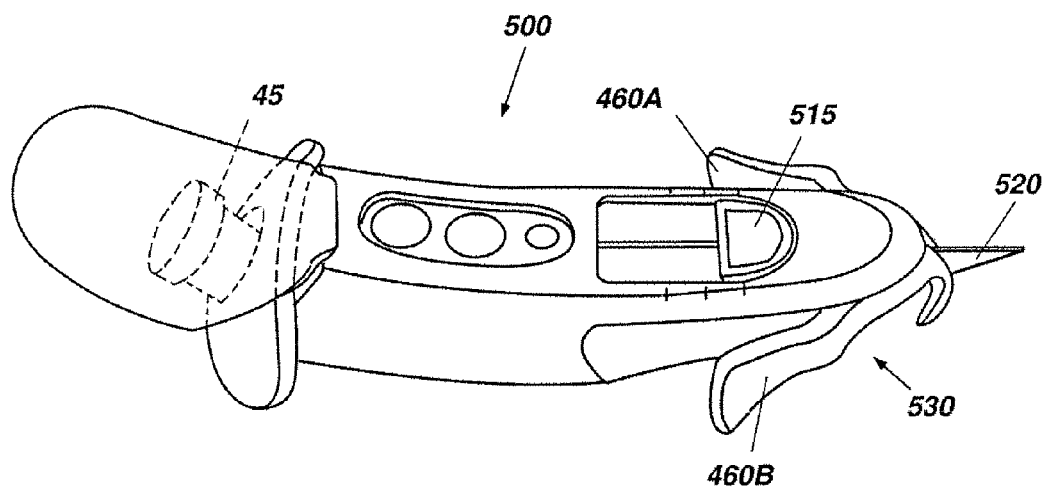
Figure 14D:
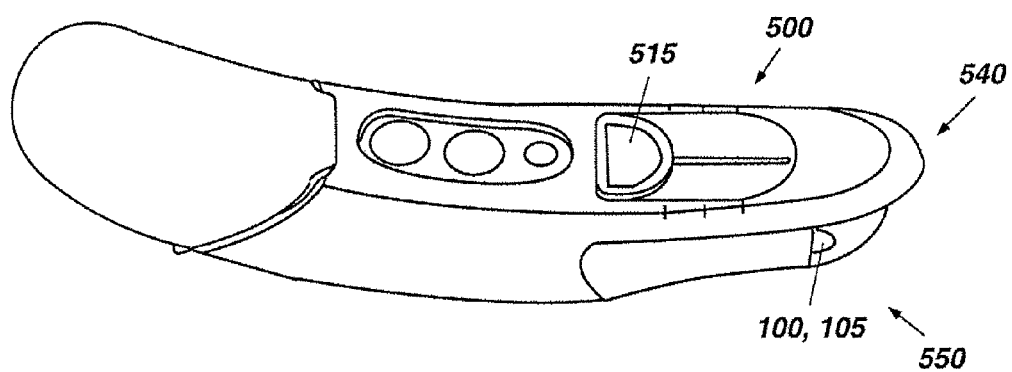

Recessed areas 535 may be provided on each side of the housing 505 for grip and hook finger tab compression of each of the tissue spreader legs 460A, 460B. In one embodiment of the present invention, each leg 460A, 460B rotates approximately 20+ degrees (FIG. 14B). In this regard, an LED lens 540 may be provided having an integrally molded locating support boss 545 for rotating the depth guard/"hook"/tissue spreader 530 and further includes detents 550 for identifying the plurality of angle openings for each leg 460A and 460B.

FIGS. 15A-15F show a compact, hand-held, ergonomically designed, stand-alone device 600 having a combination tracheal "hook" 605 and tissue-spreader/dilator 610 integrally formed therein. The combination tool 600 is of a generally durable, sterilizable, single-piece injection molded construction. As shown in the figures, the combination device 600 includes an elongated body 615 having a tracheal "hook" 605 at one end and a curved "trosseau" style dilator 610 with a bifurcated "slide-ratchet" track 620 for opening and closing the dilator or tissue spreader tips or tines 625A, 625B positioned at the opposite end of the device 600.

In this regard, the "slide-ratchet" track 620 may further include an actuator handle 630, a "scissors" shaped gripping means in one embodiment, having an attached post 635 for operable engagement with the track 620 to incrementally open and close the dilator 610. The post 635 provides for ratcheted/notched engagement of the actuator handle 630 with corresponding detents or notches 640 positioned along opposite sides 645, 646 of the bifurcated track 620. In this regard, as the handle 630 is moved along the track 620 in one direction the dilator 610 is incrementally opened. When the handle 630 is moved along the track 620 in the opposite direction the dilator 610 is incrementally closed.

As indicated in the figures, in one embodiment, the overall length of the device 600 is approximately 5.5 inches (FIG. 15A), while the closed or "neutral" static state width of the dilator 610 is approximately 0.130 inches (FIG. 15B) and the maximum opened state of the dilator is approximately 0.625 inches (FIG. 15C). Persons of ordinary skill in the art will understand that these dimensions are for illustrative purposes and that these and other dimensions shown in the figures may be varied depending on a various factors.

FIGS. 16-19 show another embodiment of a durable, compact, lightweight, ergonomic hand-held device having universal and common components and methodology of execution for use in, among other things, one-hand operation in providing an opening into the body such as in establishing an airway in medical procedures.

The device 700 includes a housing 705 having first and second sidewalls 706a, 706b connected or joined together along a centerline for housing therebetween various elements of the device 700.

The device 700 further includes a first slider unit 710 for extending and retracting a scalpel 711, and a second slider unit 720 for extending and retracting a bifurcated tissue spreader 721. In this regard, the scalpel 711 is operably connected to its respective slider unit 710 by well-known means such as those methods use to retain the blade of a box cutter. In this regard, the scalpel may include an orifice or cutout (not shown) for mating with a correspondingly shaped protrusion 719 formed in the first slider unit 710.

The bifurcated tissue spreader 721 includes a first elongated arm 722 and a second elongated arm 723 each having a hollow barrel 722a, 723a formed at one end of the respective first and second elongated arms 722, 723. The hollow barrels 722a, 723a are position atop each other and between upper and lower portions of a "C" section 724 formed in the second slider unit 720 where a retaining pin 726 positioned through the hollow barrels 72a, 723a holds the first and second elongated arms 722, 723 of the tissue spreader 721 in place in the second slider unit 720. In one embodiment, the first and second elongated arms 722, 723 of the tissue spreader 721 may each include a "hooked" distal portion 717a, 717b.

In a retracted position the scalpel 711 and tissue spreader 721 are disposed or stored safely and conveniently within the housing 705. The first slider unit 710 and the second slider unit 720 are positioned within a slider track 730 formed in the first and second sidewalls 706a, 706b. The slider track 730 permits the scalpel 711 and tissue spreader 721 to be extended away from the housing 705 and retracted toward the housing 705. In other words, in one embodiment, the device 700 described herein provides for retractable deployment, i.e., extension and retraction of a scalpel 711 and a tissue spreader 721 along a common slider track 730.

In one embodiment, the first or scalpel slider unit 710 is positioned forward of the second or tissue spreader slider unit 720 within the slider track 730 for retractable deployment from the same side/end (first end 707a) of the device 700. A spring or similar tensioning device 725 is operably connected to the first slider unit 710 along a hooked protrusion 727 and to one of the first or second sidewalls 706a, 706b to apply tension to the first slider switch 710 while in the extended position. In this regard, as explained below, in one embodiment the first slider unit 710 is moved along the slider track 730 to extend and lock the scalpel 711 into position from the housing 705. The second slider unit 720 is then moved along the slider track 730 in the same direction and as the first slider switch 710 to auto-retract the scalpel 711 while simultaneously extending and spreading the bifurcated tissue spreader 721.

In this regard, the term "auto-retract" is understood to mean that a single action (movement of the second slider unit 720 and its corresponding tissue spreader 721) causes a second action (retraction of the first slider unit 710 and its associated scalpel 711) to occur. (In actuality, as explained below, movement of the second slider unit 720 further causes a third action, that is, the spreading apart of the arms 722, 723 of the tissue spreader 721 to occur.) Accordingly, under one set of conditions, the structural configuration and positioning of the first slider unit 710 and the second slider unit 720 on the same slider track 730 results in a "cause and affect" relationship between the two units 710, 720 without any need for further manipulation, adjustment, movement, etc., from any other structural element. In other words, movement of the second slider unit 720 causes the first slider unit 710 to retract as a result of the attached spring (725) returning to its normal "relaxed" state.

Figure 17:
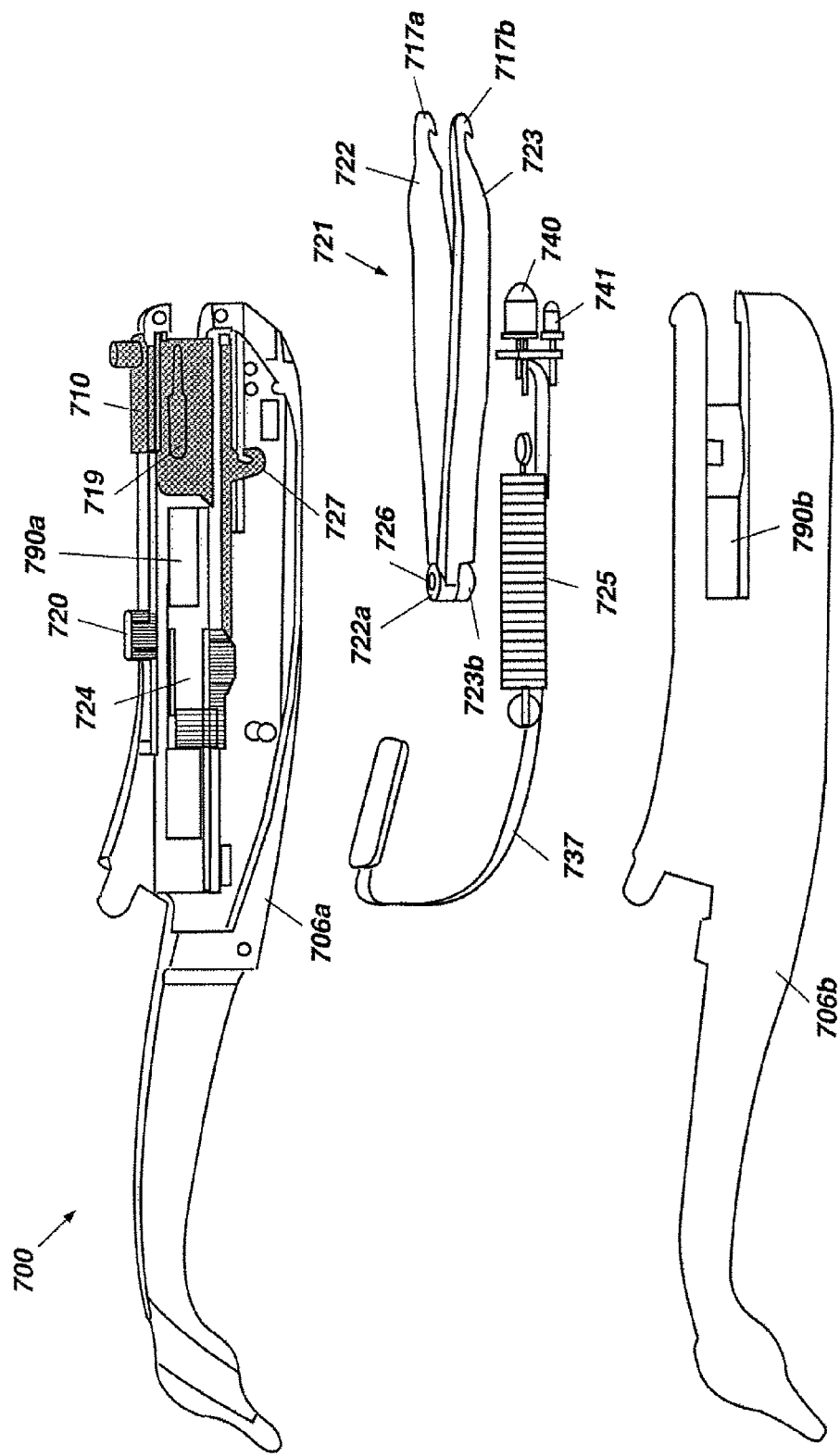
Figure 18:
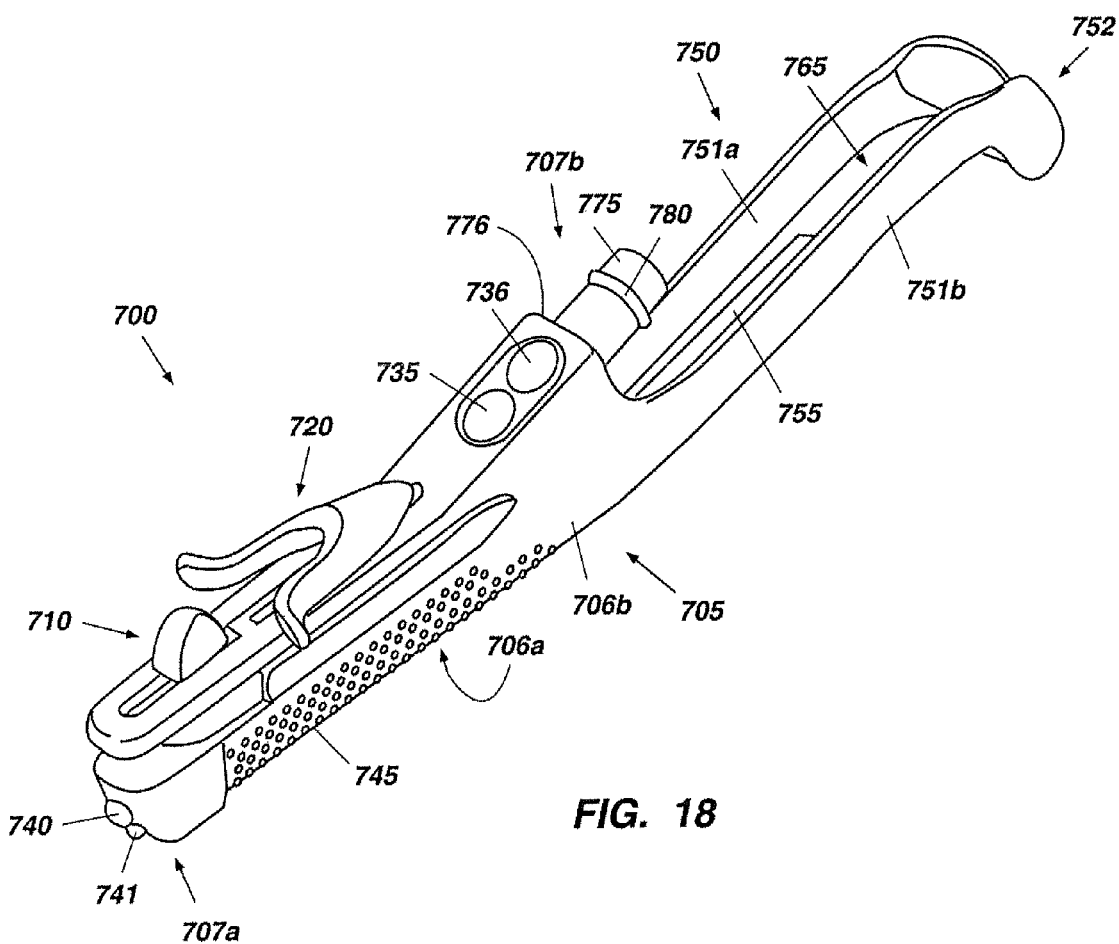
Figure 19:
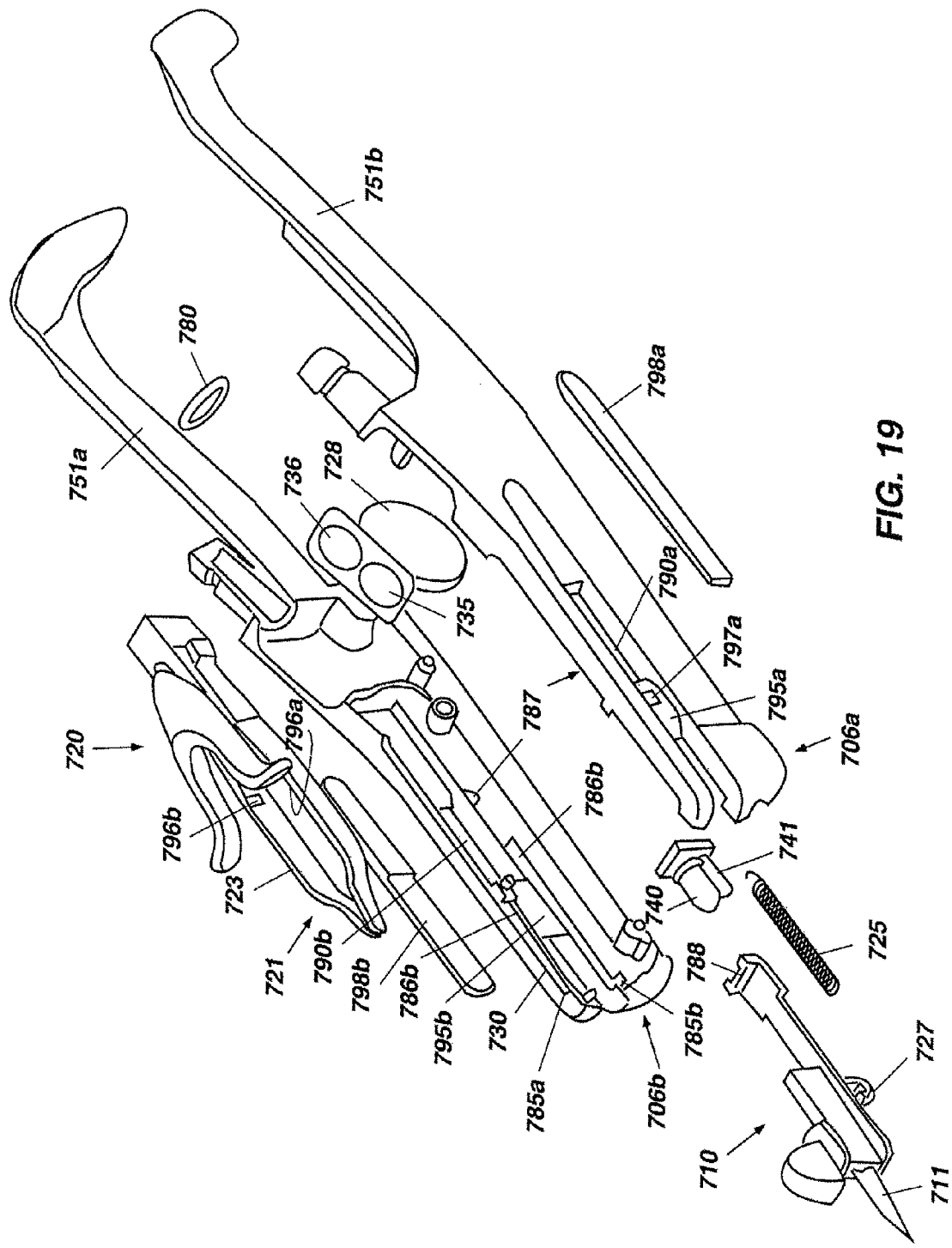

As further shown in FIGS. 18 and 19, the housing 705 also provides for switch and/or pushbutton 735, 736 activation and verification of IR (infrared) and visible light spectrum LEDs 740, 741 mounted on the front-underside of the housing 705. Lithium ion batterie(s) 728 are positioned within the housing 705 to provide power to the LEDs 740, 741. The pushbuttons 735, 736 and batteries are electrically connected to the LEDs 740, 741 via a printed circuit board (PCB) or ribbon 737, as shown in FIG. 17.

Figure 16:
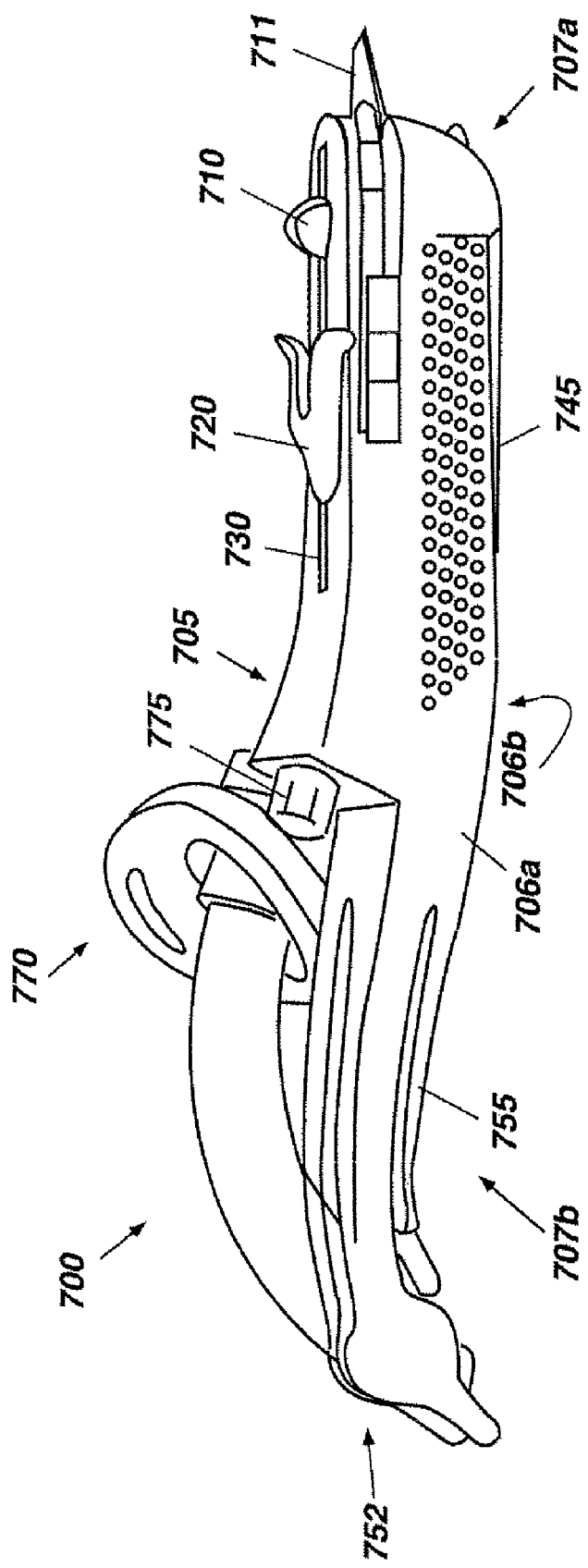
FIGS. 16-19 and 20A-20D show an apparatus for providing a passage into the body in accordance with still another embodiment.

"Gripper nubs" (raised bumps) 745, shown in FIG. 16, may be molded into the housing 705 or formed from rubber and applied to the housing 705 to provide a textured surface to assist the user in holding, gripping, or otherwise maneuvering the device 700.

As shown in FIG. 18, the device 700 may further include an elongated carriage 750 formed from the joined together sidewalls 706a, 706b of the device 700 and a protruding clip 755 each extending from a second end 707b opposite the first end 707a of the device 700. In this regard, the protruding clip 755 is positioned in close proximity to the underside of the sidewalls 706a, 706b such that prep wipes (not shown) may be retained between the protruding clip 755 and the underside of the sidewalls 706a, 706b.

The elongated carriage 750 having spaced apart sides 751a, 751b and the protruding clip 755 form or define an open-well or compartment 765 for retaining an airway tube 770 (FIG. 16) and sterile gaze (not shown). In this regard, the carriage 750 further includes a curved distal portion 752 formed by the spaced apart sides 751a, 751b. The distal portion 752 of the carriage 750 is shaped to correspond to the shape of the airway tube 770 retained therebetween and may further be configured to allow the distal portion 752, i.e., spaced apart sides 751a, 751b to flex apart and return to their original position due to material memory to assist in holding one end of airway tube 770 in place. A retaining or mounting stem 775 having an O-ring 780 positioned around the mounting stem 775 may further be included and positioned along an upper area 776 of the device 700 to assist in holding the opposite end of the airway tube 700 in place.

Figure 20A:
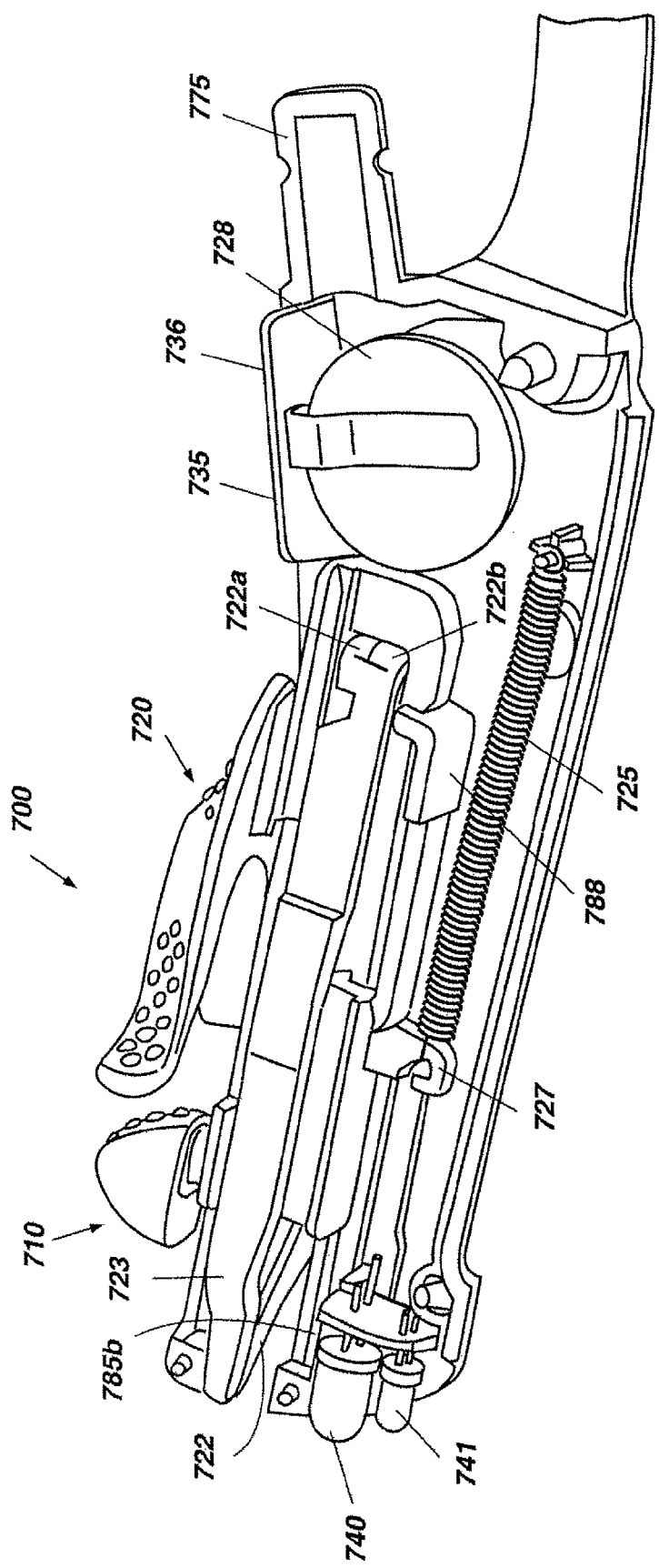
Figure 20B:
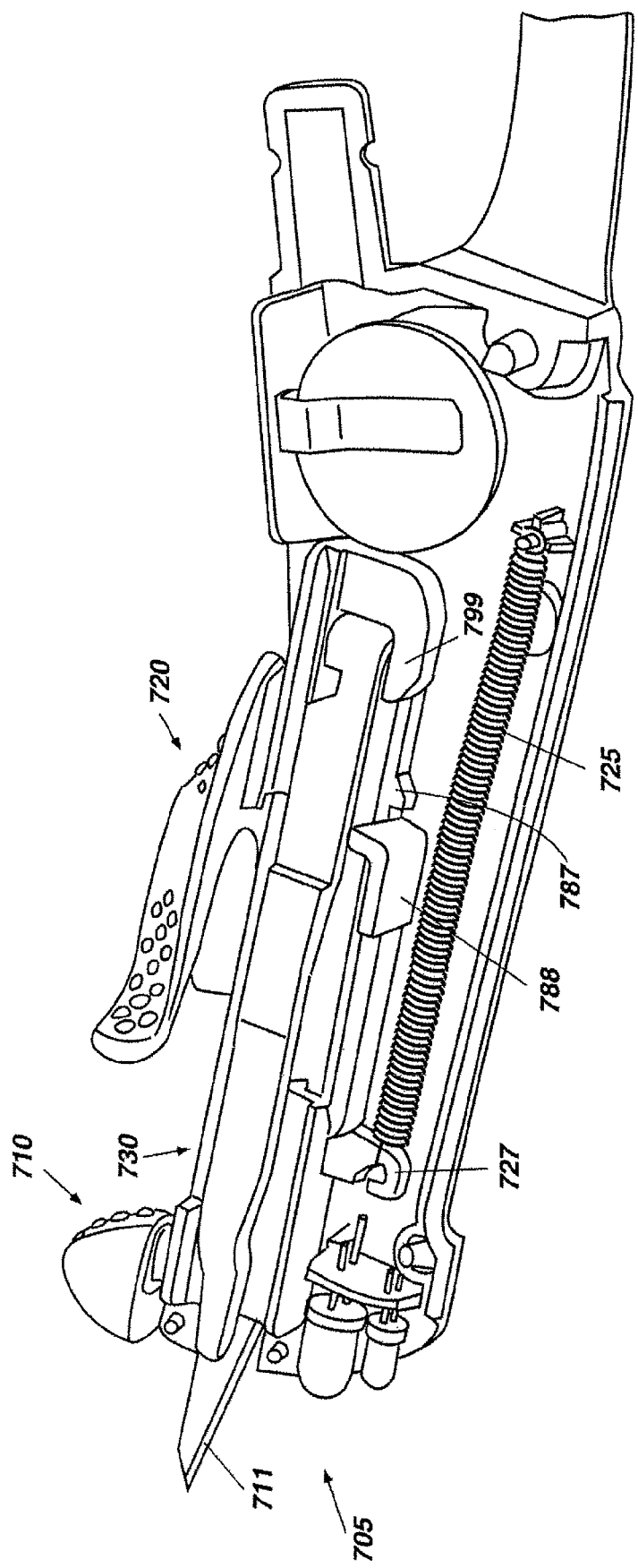

As indicated above and shown in FIGS. 20A and 20B, the device 700 includes a first slider unit 710 for extending and retracting a scalpel 711, and a second slider unit 720 for extending and retracting a bifurcated tissue spreader 721 along a common slider track 730 formed between first and second sidewalls 706a, 706b of the housing 705 to permit for retractable deployment and retraction of a scalpel 711 and a tissue spreader 721 from the same side of the device 700.

As shown in FIG. 20B, the first slider unit 710 having the scalpel 711 attached thereto is moved in a forward direction along the slider track 730 to extend the scalpel 711 from the housing 705. In this regard, as best shown in FIG. 19, the first slider unit 710 is movably retained within an elongated top rail 786a and a corresponding elongated bottom rail 786b of the slider track 730 formed in each of the first and second sidewalls 706a, 706b to permit movement of the first slider switch 710 along the slider track 730 until the first slider unit 710 is position between an upper forward portion 785a of the top rail 786a and a bottom forward portion 785b of the bottom rail 786b of each side of the slider track 730, and a retaining nub 787 (FIG. 20B) having a curved rearward surface formed on an outside surface of each of the bottom rails 786b formed in respective sidewalls 706a, 706b. In this regard, the first slider unit 710 is retained in the forward position, despite tension from the spring 725 having been extended due to the forward movement of the first slider unit 710 along the slider track 730, by an "L" shaped retaining lip 788 located at one end of the first slider unit 710 being positioned against the retaining nubs 787. In this regard, the curved surface of the retaining nubs 787 permits the retaining lip 788 to be easily pushed passed the retaining nubs 787 when moved in a forward direction, but held relatively securely when attempting to move in the backward or rearward direction by a relatively flat surface back surface of the retaining lip 788. As such, the first slider unit 710 is retained in the forward position along the slider track 730 with the scalpel 711 extended.

In one embodiment, once the first slider unit 710 is retained in the forward position the second slider unit 720 is moved in the forward direction to extend and expand the first elongated arm 722 and the second elongated arm 723 of the bifurcated tissue spreader 721, and to facilitate auto-retraction/release of the first slider unit 710.

Figure 20C:
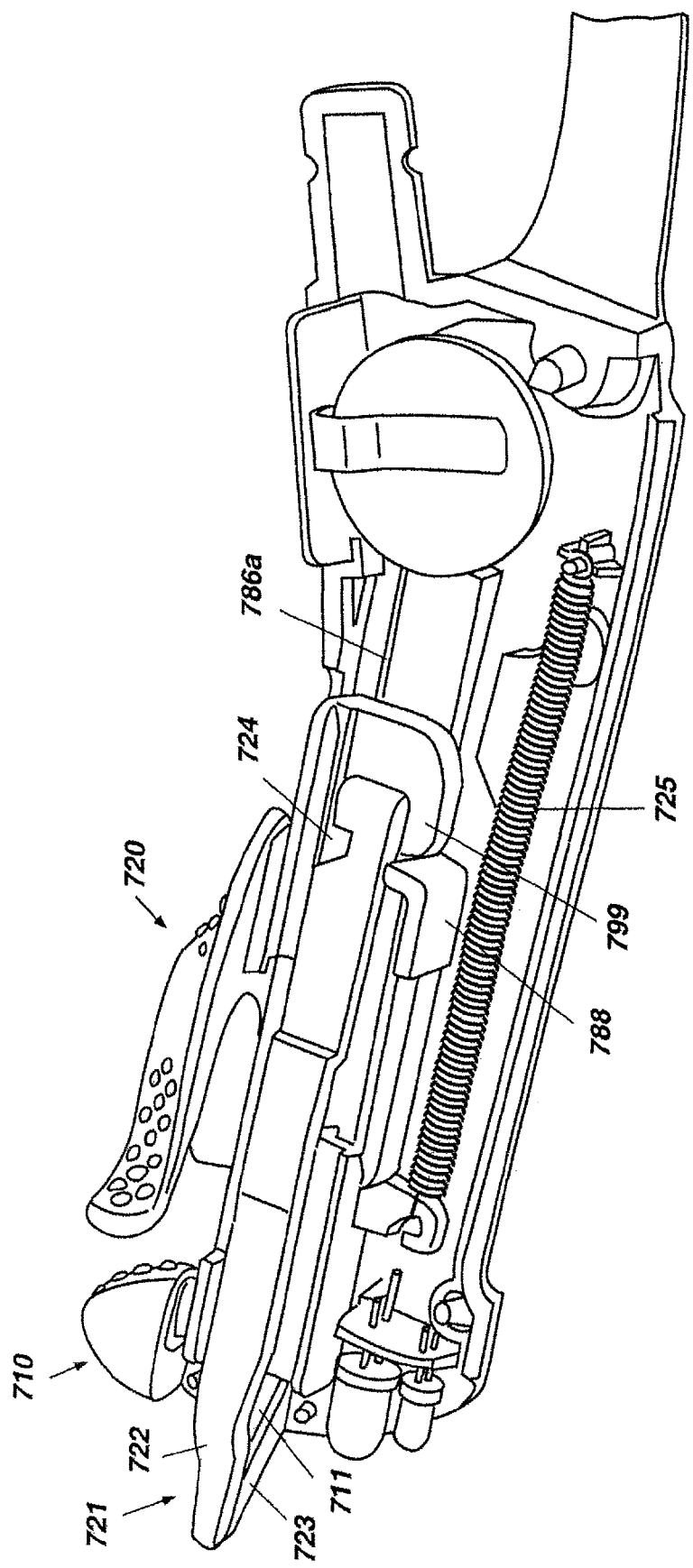
Figure 20D:
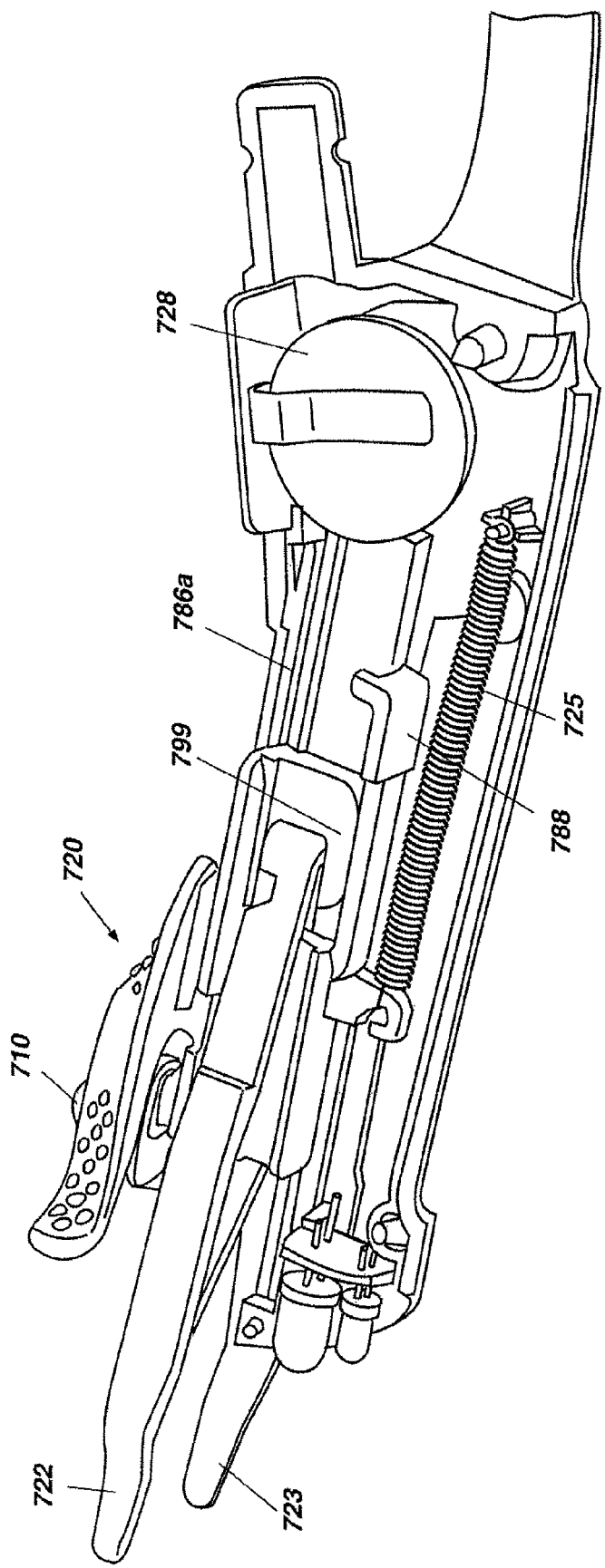

In this regard, as shown in FIGS. 19, 20C and 20D, the second slider switch 720 is movably retained within the elongated top rail 786a of the slider track 730 formed in each of the first and second sidewalls 706a, 706b to permit movement of the second slider unit 720 along the slider track 730. As indicated above, the first elongated arm 722 and the second elongated arm 723 of the bifurcated tissue spreader 721 are retained within the "C" section 724 formed in the second slider unit 720. The first elongated arm 722 and the second elongated arm 723 of the bifurcated tissue spreader 721 are further positioned such that one of the elongated arms 722, 723 extends from inside the housing 705 through a first window 790a formed in one of the sidewalls 706a, 706b, and the other elongated arm 722, 723 extends from inside the housing 705 through a second window 790b opposite the first window 790a to position each of the elongated arms 722, 723 on opposite sides of the device 700.

When moved in the forward direction along the slider track 730 a first lateral sidewall portion 795a formed between the top rail 786a and the bottom rail 786b of the slider track 730 of the first sidewall 706a, and a second lateral sidewall portion 795b formed between the top rail 786a and the bottom rail 786b of the slider track 730 of the second sidewall 706b force the first elongated arm 722 and the second elongated arm 723 apart (FIG. 20D) as the first and second lateral sidewall portions 795a, 795b approach the "C" section 724 formed in the second slider unit 720 (connection point of the first elongated arm 722 and the second elongated arm 723 of the bifurcated tissue spreader 721). In one embodiment, the first and second elongated arm 722, 723 are displaced or spread apart approximately 13 mm.

As the first and second elongated arms 722, 723 are moved along and therefore spread apart by the respective first and second lateral sidewall portions 795a, 795b a first indented portion 796a of the first elongated arm 722 contacts a first protrusion 797a formed on the first lateral sidewall portion 795a. Likewise, a second indented portion 796b of the second elongated arm 723 contacts a second protrusion (not shown) formed on the second lateral sidewall portion. The bifurcated tissue spreader 721 is retained in this forward position by a first elongated tension strip 798a formed in the first sidewall 706a and biased against the first elongated arm 722, and a second elongated tension strip 798b formed in the second sidewall 706b and biased against the second elongated arm 723.

Movement of the second slider unit 720 in the backward or rearward direction is accomplished by manually applying sufficient force to the second slider unit 720 in the backward direction to overcome the bias force applied by the first and second elongated tension strips 798a, 798b.

As indicated above, forward movement of the second slider unit 720 facilitates auto-retraction of the first slider unit 710. In this regard, when the first slider unit 710 is retained in the forward position along the slider track 730 with the scalpel 711 extended and the second slider unit 720 is move in the forward direction, a curved shaped lower segment 799 of the "C" section 724 of the second slider unit 720 contacts and forces the retaining lip 788 of the first slider unit 710 to disengage from the retaining nubs 787 as the second slider unit 720 moves past the retaining lip 788 forcing the retaining lip 788 downward to permit the spring 725 to move the first slider unit 710 back to its original position within the housing 705 with the scalpel 711 safely retracted (FIG. 20D).

Forward and backward directional movement of the second slider unit 720 may be accomplished independent of the first slider unit 710 and may be accomplished regardless of the position of the first slider unit 710 along the slider track 730.

Although methods are described and illustrated herein with steps occurring in a certain order, the specific order of the steps, or any continuation or interruption between steps, is not required.

The apparatus and methods have been described with some particularity, but the specific designs, constructions and steps disclosed are not to be taken as delimiting. Obvious modifications will make themselves apparent to those of ordinary skill in the art, all of which will not depart from the essence and spirit of the subject matter described herein and all such changes and modifications are intended to be encompassed within the appended claims.

What is claimed is:

1. An apparatus for providing a passage into the body, comprising:
a housing;
a slider track formed within the housing; and
a first slider unit configured to retain a scalpel and a second slider unit configured to retain a tissue spreader each operably connected to the slider track for movement along the slider track.

2. The apparatus of claim 1, wherein movement of the first slider unit and the second slider unit along the slider track permits retractably deployment of the scalpel and the tissue spreader from the housing.

3. The apparatus of claim 2, where retractable deployment of the scalpel and the tissue spreader are from the same side of the housing.

4. The apparatus of claim 3, wherein retractable deployment of the tissue spreader causes auto-retraction of the scalpel.

5. The apparatus of claim 1, wherein the tissue spreader includes a first arm and a second arm connected together and structured to move from a closed position to an open position when the second slider unit is moved along the slider track.

6. The apparatus of claim 5, wherein the first slider unit is positioned between the first arm and the second arm of the tissue spreader.

7. The apparatus of claim 6, wherein retractable deployment of the scalpel and tissue spreader are from the same side of the housing.

8. The apparatus of claim 1, wherein the first slider unit, the second slider unit, and the slider track are configured to permit auto-retraction of the first slider unit when the second slider unit is moved along the slider track.

9. An apparatus for providing a passage into the body having a first slider unit and a second slider unit are each operably connected to a common slider track for retractable deployment of a scalpel and a tissue spreader attached respectively thereto, and for the auto-retraction of the scalpel due to movement of the second slider unit.

10. A device for providing a passage into the body, comprising:
   a first slider unit configured to permit retractable deployment of a scalpel; and
   a second slider unit configured to retain a tissue spreader, wherein movement of the second slider unit causes the first slider unit to auto-retract.

11. The device of claim 10, wherein the second slider unit permits retractable deployment of the tissue spreader.

12. The device of claim 11, wherein the first slider unit and the second slider unit are each operably connected to a common slider track.

13. The device of claim 12, wherein the first slider unit and the second slider unit permit retractable deployment of the scalpel and the tissue spreader from the same side of the device.

14. A method for providing a passage into the body, comprising the steps of:
   deploying a scalpel along a slider track formed within a device;
   making an incision with the scalpel in an incision site; and
   deploying a tissue spreader along the slider track to open the incision, wherein deploying the tissue spreader causes auto-retraction of the scalpel.

15. The method of claim 14, wherein the scalpel and the tissue spreader are deployed from the same side of the slider track.

16. The method of claim 15, further including the steps of:
   inserting a breathing tube into the incision opened by the tissue spreader; and
   removing the tissue spreader from the incision site.

17. The method of claim 16, further including the steps of:
   securing a retainer strap to the breathing tube to secure the breathing tube in place.

* * * * *

UNITED STATES PATENT AND TRADEMARK OFFICE
CERTIFICATE OF CORRECTION

PATENT NO. : 8,356,598 B2  
APPLICATION NO. : 12/043849  
DATED : January 22, 2013  
INVENTOR(S) : Royce Rumsey Page 1 of 1

It is certified that error appears in the above-identified patent and that said Letters Patent is hereby corrected as shown below:

In the Specification

Column 1, line 4, insert the following paragraph immediately after the title of the application and before the heading CROSS-REFERENCE TO RELATED APPLICATION:

--This invention was made with government support under Contract No. W81XWH-07-01-0652 awarded by US Army Medical Research Acquisition Activity. The government has certain rights in the invention.--

Signed and Sealed this
Eighteenth Day of August, 2015

Michelle K. Lee
*Director of the United States Patent and Trademark Office*